(12) United States Patent
Zasloff

(10) Patent No.: US 8,623,416 B2
(45) Date of Patent: Jan. 7, 2014

(54) FORMULATIONS COMPRISING AMINOSTEROLS

(76) Inventor: Michael Zasloff, Merion, PA (US)

( * ) Notice: Subject to any disclaimer, the term of this patent is extended or adjusted under 35 U.S.C. 154(b) by 244 days.

(21) Appl. No.: 12/953,083

(22) Filed: Nov. 23, 2010

(65) Prior Publication Data

US 2011/0123624 A1   May 26, 2011

Related U.S. Application Data

(60) Provisional application No. 61/264,499, filed on Nov. 25, 2009.

(51) Int. Cl.
*A61K 9/14* (2006.01)
*A61K 39/395* (2006.01)
*A61K 39/00* (2006.01)
*A61K 39/38* (2006.01)

(52) U.S. Cl.
USPC ............. 424/489; 424/130.1; 424/184.1

(58) Field of Classification Search
USPC .......................................... 424/489
See application file for complete search history.

(56) References Cited

U.S. PATENT DOCUMENTS

| | | | |
|---|---|---|---|
| 3,773,919 A | 11/1973 | Boswell et al. |
| 4,544,545 A | 10/1985 | Ryan et al. |
| 5,021,234 A | 6/1991 | Ehrenfeld |
| 5,192,756 A | 3/1993 | Zasloff et al. |
| 5,637,691 A | 6/1997 | Frye et al. |
| 5,721,226 A | 2/1998 | Frye et al. |
| 5,733,899 A | 3/1998 | Frye et al. |
| 5,763,430 A | 6/1998 | Zasloff |
| 5,792,635 A | 8/1998 | Zasloff |
| 5,795,885 A | 8/1998 | Zasloff et al. |
| 5,834,453 A | 11/1998 | Regen |
| 5,840,740 A | 11/1998 | Zasloff et al. |
| 5,840,936 A | 11/1998 | Zasloff et al. |
| 5,847,172 A | 12/1998 | Zasloff et al. |
| 5,856,535 A | 1/1999 | Zasloff et al. |
| 5,874,597 A | 2/1999 | Jones |
| 5,994,336 A | 11/1999 | Zasloff et al. |
| 6,017,906 A | 1/2000 | Mintz et al. |
| 6,143,738 A | 11/2000 | Zasloff |
| 6,147,060 A | 11/2000 | Zasloff et al. |
| 6,388,108 B1 | 5/2002 | Rao et al. |
| 6,596,712 B2 | 7/2003 | Zasloff et al. |
| 6,962,909 B2 | 11/2005 | Zasloff et al. |
| 2004/0033267 A1 | 2/2004 | Merisko-Liversidge et al. |
| 2004/0077601 A1* | 4/2004 | Adams et al. ............... 514/64 |
| 2005/0261508 A1 | 11/2005 | Zasloff et al. |
| 2006/0166950 A1 | 7/2006 | Zasloff et al. |
| 2006/0183928 A1 | 8/2006 | Zasloff et al. |
| 2007/0010504 A1 | 1/2007 | Chellquist et al. |
| 2008/0241252 A1* | 10/2008 | Lyons et al. ............ 424/489 |

FOREIGN PATENT DOCUMENTS

| | | |
|---|---|---|
| DE | 32 18 121 A1 | 11/1983 |
| EP | 0 036 676 | 9/1981 |
| EP | 0 058 481 B2 | 8/1982 |
| EP | 088 046 | 9/1983 |
| EP | 0 102 324 | 3/1984 |
| EP | 0 142 641 | 5/1985 |
| EP | 0 143 949 | 6/1985 |
| EP | 1800666 A1 * | 6/2007 |
| JP | 58-118008 | 7/1983 |
| WO | WO 96/08270 | 3/1996 |
| WO | WO 98/17281 | 4/1998 |
| WO | WO 98/30213 | 7/1998 |
| WO | WO 98/50347 | 11/1998 |
| WO | WO 98/54366 | 12/1998 |
| WO | WO 99/49830 | 10/1999 |
| WO | WO 99/56764 | 11/1999 |
| WO | WO 99/66936 | 12/1999 |

OTHER PUBLICATIONS

ArtUnion. "List of inorganic acids (mineral acids), chemical formulas, anions and salts". [Retrieved Dec. 31, 2012]. Retrieved from the internet <URL: http://www.reagent.lv/HOMEPAGE/About/list-of-inorganic-acids.php>.*

International Search Report and Written Opinion cited in related International Patent Application No. PCT/US2010/057754, completed Aug. 9, 2011.

International Preliminary Report on Patentability cited in related International Patent Application No. PCT/US2010/057754, mailed Jun. 7, 2012.

* cited by examiner

*Primary Examiner* — Robert T Crow
*Assistant Examiner* — Doan Phan
(74) *Attorney, Agent, or Firm* — Foley & Lardner LLP

(57) ABSTRACT

This invention relates to stable aminosterol phosphate compositions. The aminosterol phosphate compositions permit administration without associated tissue damage and achieve a sustained release effect.

15 Claims, 9 Drawing Sheets
(6 of 9 Drawing Sheet(s) Filed in Color)

Figure 3
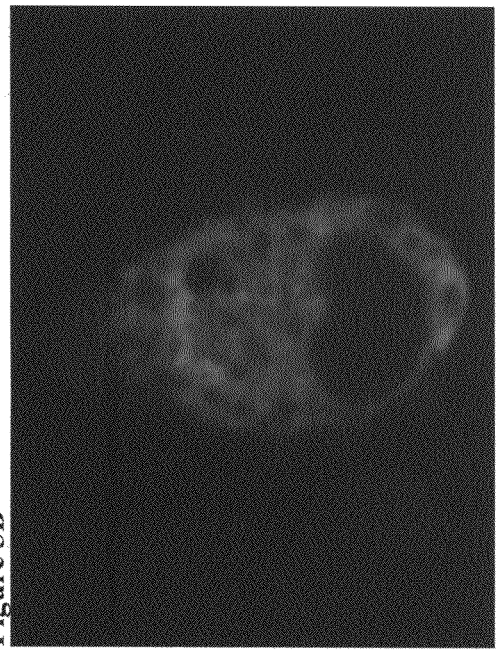
Figure 3B
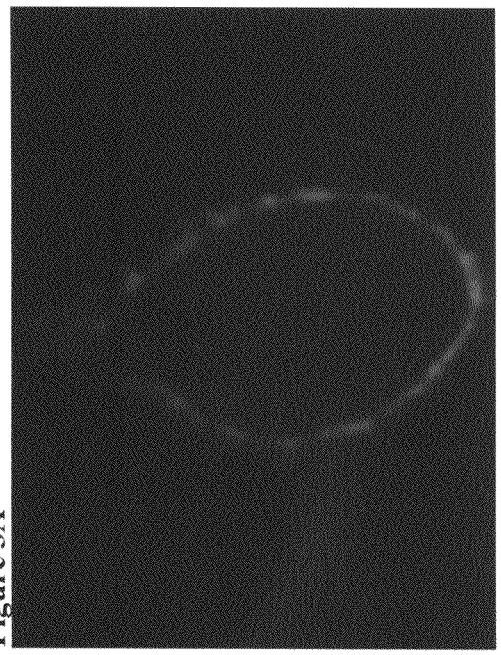
Figure 3A

Figure 7

*In vitro* antiviral activity of squalamine against Dengue, as studied in a human endothelial cell line

FORMULATIONS COMPRISING AMINOSTEROLS

CROSS-REFERENCE TO RELATED APPLICATIONS

This application claims priority of U.S. Provisional Patent Application No. 61/264,499, filed on Nov. 25, 2009. The contents of that application is incorporated herein by reference in its entirety.

FIELD OF THE INVENTION

This invention relates to stable aminosterol phosphate compositions. The aminosterol phosphate compositions permit administration without associated tissue damage and achieve a sustained release effect.

BACKGROUND OF THE INVENTION

A. Background Regarding Squalamine

The discovery of squalamine, a water soluble compound, the structure of which is shown below, was reported by Michael Zasloff in 1993 (U.S. Pat. No. 5,192,756). Squalamine was discovered in various tissues of the dogfish shark (*Squalus acanthias*) in a search for antibacterial agents. The most abundant source of squalamine is in the livers of *Squalus acanthias*, though it is found in other sources, such as lampreys (Yun et al., "Identification of Squalamine in the Plasma Membrane of White Blood Cells in the Sea Lamprey," *Petromyzon marinus*," *J. Lipid Res.*, 48(12): 2579-2586 (2007)).

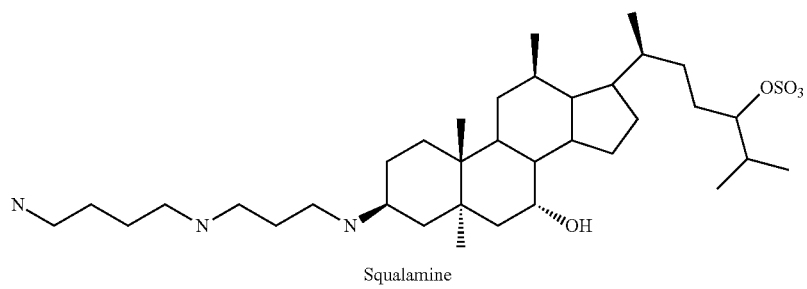

Squalamine

Chemically squalamine presented a structure never before seen in nature that being a bile acid coupled to a polyamine (spermidine); i.e., a steroid chemically linked to a polyamine. The chemical structure of squalamine, also known as 3 beta-N-1-(N-[3-(4-aminobutyl)]-1,3-diaminopropane)-7 alpha,24 zeta-dihydroxy-5 alpha-cholestane 24-sulfate, has been determined by fast atom bombardment mass spectroscopy and NMR. Squalamine is a cationic steroid characterized by a condensation of an anionic bile salt intermediate with spermidine.

Squalamine and structurally related aminosterols, such as Aminosterol 1436, have potentially valuable applications in the treatment and or prevention of disease (Sills, Williams et al. 1998; U.S. Pat. No. 5,763,430; Ahima, Patel et al. 2002; U.S. Pat. Nos. 6,596,712; 6,962,909; Connolly, Desai et al. 2006). Aminosterol 1436, also known as MSI 1436, is chemically known as (3beta-N-1(spermine)-7alpha, 24R-dihydroxy-5alpha-cholestane 24-sulfate). The structure of Aminosterol 1436 is shown below.

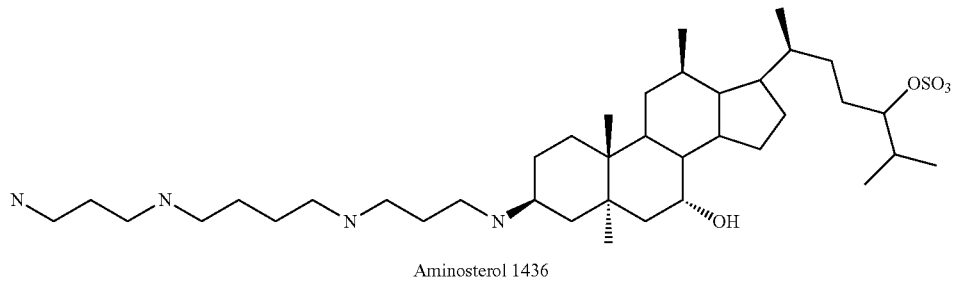

Aminosterol 1436

1. Known Activities of Squalamine and Aminosterol 1436

Numerous studies later demonstrated that squalamine exhibits potent antibacterial activity in vitro (Salmi, Loncle et al. 2008). Subsequently, squalamine was discovered to exhibit antiangiogenic activity in vitro and upon administration to animals (Sills, Williams et al. 1998; Yin, Gentili et al. 2002). As a consequence, squalamine has been evaluated in disease states known to be associated with pathological neovascularization, such as cancer (Sills, Williams et al. 1998; Schiller and Bittner 1999; Bhargava, Marshall et al. 2001; Williams, Weitman et al. 2001; Hao, Hammond et al. 2003; Herbst, Hammond et al. 2003; Sokoloff, Rinker-Schaeffer et al. 2004), and vascular disorders of the eye, including macular degeneration (US2007/10504A1 2007), retinopathy of prematurity (Higgins, Sanders et al. 2000; Higgins, Yan et al. 2004; US2007/10504A1 2007), corneal neovascularization (Genaidy, Kazi et al. 2002) and diabetic retinopathy (US2007/10504A1).

For example, Ahima (2002) teaches that Aminosterol 1436 decreases body weight, specifically fat, by suppressing feeding and preventing the reduction in energy expenditure, hormonal changes, and patterns of neuropeptide expression normally associated with weight loss. This reference concludes that Aminosterol 1436 acts in the brain to regulate food intake and energy expenditure, likely through suppression of orexigenic hypothalamic pathways.

The utility of squalamine as an anti-infective has been demonstrated in vitro against bacteria and fungi (Moore, Wehrli et al. 1993; Rao, Shinnar et al. 2000; Salmi, Loncle et al. 2008). Squalamine is a cationic amphipathic substance exhibiting an affinity for membranes composed of anionic phospholipids (Selinsky, Zhou et al. 1998; Selinsky, Smith et al. 2000). Like other such agents, including magainin and other cationic antimicrobial peptides, squalamine is believed to exert antimicrobial action by interacting electrostatically with the membranes of target microorganisms, which generally display anionic phospholipids on the membrane surface exposed to the environment, subsequently disturbing their functional integrity, and causing death of the targeted microbe (Sills, Williams et al. 1998; Zasloff 2002; Salmi, Loncle et al. 2008).

To date, squalamine has not been reported to display efficacy as an anti-infective in a living animal. In no published patent application or issued patent has such evidence been reported (U.S. Pat. Nos. 5,192,756; 5,637,691; 5,721,226; 5,733,899; 5,763,430; 5,792,635; 5,795,885; 5,840,740; 5,840,936; 5,847,172; 5,856,535; 5,874,597; 5,994,336; 6,017,906; 6,143,738; 6,147,060; 6,388,108; 6,596,712; U.S. Patent Publication No. 2005/0261508A1 2005; U.S. Pat. No. 6,962,909; U.S. Patent Publication No. 2006/0166950A1 2006; U.S. Patent Publication No. 2006/0183928A1 2006; U.S. Patent Publication No. 2007/10504A1 2007).

Recent studies have revealed that squalamine is inactivated by the concentrations of ionized calcium and magnesium present in mammalian blood, preventing squalamine from exerting its antimicrobial activity in the setting of systemic bacterial, fungal, or protozoan infections (Salmi, Loncle et al. 2008).

Most studies of mechanism of squalamine have focused on the effects of squalamine on properties of the endothelial cell. The compound has been shown to inhibit many downstream effects stimulated by diverse growth-factors (VEGF, thrombin, FGF) including cellular proliferation, cellular migration, vascular tube formation, sodium-proton anti-porter activation. (Sills et al., "Squalamine inhibits angiogenesis and solid tumor growth in vivo and perturbs embryonic vasculature," Cancer Res 58, 2784-92 (1998); Li et al., "Squalamine and cisplatin block angiogenesis and growth of human ovarian cancer cells with or without HER-2 gene overexpression," Oncogene 21, 2805-14 (2002); Akhter et al., "Squalamine, a novel cationic steroid, specifically inhibits the brush-border Na+/H+ exchanger isoform NHE3," Am J Physiol 276, C136-44 (1999); and Williams et al., "Squalamine treatment of human tumors in nu/nu mice enhances platinum-based chemotherapies," Clin Cancer Res 7, 724-33 (2001)).

No mention of squalamine's use as a systemic antimicrobial agent, for example, appears in a recent patent application (U.S. Patent Publication No. 2007/10504A1), which describes a favored salt form of squalamine for therapeutic administration, and which addresses the utility of squalamine as a systemic agent in the treatment of disorders of neovascularization and cancer.

To date, no published data describe or support the efficacy of squalamine in treating or preventing a systemic viral infection in an animal. It has been reported in a patent application that squalamine could inhibit the infectivity of HIV and HSV in tissue culture (WO96/08270). However, it was not reported at that time, nor until the invention disclosed herein, that squalamine could exhibit antiviral activity when administered systemically to an animal. In the experiments described in WO96/08270, squalamine was conceived as a component of a topical agent to be used as a "chemical condom", acting as a microbicide, and capable of rapidly inactivating HIV or HSV on contact by disrupting the outermost membranous envelopes of the viruses. Thus, the antiviral properties of squalamine observed in vitro were believed to result from direct disruption of the viral membrane, via a mechanism analogous to that proposed for its antibacterial activity. The potential use of squalamine for the topical prevention of sexually transmitted diseases such as HIV, Herpes simplex, and *Neisseria gonorrhea* was presented at the 1995 ICAAC conference (MacDonald 1995). Thus, squalamine was proposed to have utility as an advanced form of "disinfectant," to be applied to a mucosal surface in some formulation and thereby prevent viable virus from gaining access to the epithelial surfaces of the genitourinary tract.

Squalamine has been shown to inhibit a specific isoform of the sodium-hydrogen exchanger ("NHE-3"), a protein that plays a role in numerous cellular processes that involve the control of intracellular hydrogen ions (Akhter, Nath et al. 1999). As a consequence of this activity, it was proposed that squalamine might find utility in treating diseases, including viral infections, where NHE3 played a critical role, and where its inhibition (by squalamine) could be effected (see e.g., U.S. Pat. No. 6,962,909). It has been proposed that squalamine could be used to treat viral infections should it be known that a specific virus infected a target cell expressing an NHE sensitive to inhibition (NHE-3 in the case of squalamine), and that the specific NHE played a critical role in the cellular homeostasis of that cell type, and that the virus in question naturally infected that cell type in the course of a disease process (U.S. Pat. No. 6,962,909). To date, however, no example of an NHE-3 dependent viral infection has been reported in the literature, nor has any known NHE-3 inhibitor been shown to exhibit antiviral activity in an animal, including squalamine. Furthermore the viruses demonstrated to be inactivated in vitro by squalamine, namely HIV and HSV (WO96/08270) are now known to infect cells via a pathway that is "pH independent", in the sense that inhibitors of pH homeostasis do not influence infectivity (Pelkmans and Helenius 2003).

1436 is an aminosterol, isolated from the dogfish shark, structurally related to squalamine (U.S. Pat. No. 5,840,936; Rao, Shinnar et al. 2000). Aminosterol 1436 exhibits antiviral activity against HIV in tissue culture (U.S. Pat. No. 5,763,430) via a mechanism proposed to involve inhibition of a lymphocyte-specific NHE by 1436, resulting in suppression of cytokine responsiveness, and subsequent depression of the capacity of the lymphocyte to support HIV replication (U.S. Pat. No. 5,763,430). Aminosterol 1436, however, has an additional pharmacological property, not shared with squalamine, namely potent appetite suppression and promotion of dose-dependent weight loss (U.S. Pat. No. 6,143,738; Zasloff, Williams et al. 2001; Ahima, Patel et al. 2002). Administration of Aminosterol 1436 to animals at doses that would achieve tissue concentrations of Aminosterol 1436 speculated to exert an antiviral benefit cause profound weight loss and suppression of food intake and death due to starvation (Zasloff, Williams et al. 2001; Ahima, Patel et al. 2002).

Recent patents have been issued describing squalamine like compounds with potent antibacterial activity, but no mention is made of their utility as antiviral agents (U.S. Pat. Nos. 5,834,453; 6,017,906). Indeed, the potential value of squalamine and its analogs as systemic agents has been questioned due to the extensive binding to albumin exhibited by these compounds (U.S. Pat. No. 5,834,453).

Squalamine in its intravenous form, squalamine lactate, is in the process of being tested as a treatment of fibrodysplasia ossificans progressiva, a rare disease where connective tissue will ossify when damaged. (Genesis, A., "Squalamine trial for the treatment of fibrodysplasia ossificans progressiva initiated", *Angiogenesis Weekly*, 8:45 (2002).) Squalamine is also undergoing trials for treatment of non-small cell lung cancer (stage I/IIA) as well as general phase I pharmacokinetic studies. (Herbst et al., "A Phase I/IIA Trial of Continuous Five-Day Infusion of Squalamine Lactate (MSI-1256F) Plus Carboplatin and Paclitaxel in Patients with Advanced Non-Small Cell Lung Cancer 1", *Clinical Cancer Research*, 9:4108-4115 (2003); Hao et al., "A Phase I and Pharmacokinetic Study of Squalamine, an Aminosterol Angiogenesis Inhibitor", *Clin Cancer Res.*, 9(7): 2465-2471 (2003).) In 2005, the Food and Drug Administration granted squalamine Fast Track status for approval for treatment of age-related macular degeneration. (CATE: California Assistive Technology Exchange", California Assistive Technology Exchange, http://cate.ca.gov/index.cfm?a=Resources&p=News&article=176, Retrieved 2009 Mar. 31.) However, Genaera Corporation discontinued trials for the use of squalamine in treating prostate cancer and wet age-related macular degeneration in 2007. ("PROSTATE CANCER; Genaera Discontinues LOMUCIN in Cystic Fibrosis and Squalamine in Prostate Cancer Studies", *Drug Week*, pp. 251. 2007 Jul. 20; "Reports describe the most recent news from Genaera Corporation". *Biotech Business Week*, pp. 1540 (2007 Sep. 17).) Squalamine is also marketed under the brand name Squalamax™ as a dietary supplement, though it has not been approved as a drug in this form and thus cannot make therapeutic claims. Squalamax™ is an unfractionated extract of shark liver, containing innumerable uncharacterized substances in addition to squalamine, itself present below 0.01% of the total weight of the extract. ("Cyber Warning Letter", Center for Drug Evaluation and Research (2002 May 6), http://www.fda.gov/CDER/warn/cyber/2002/CFSANnuGen.htm; Retrieved 2009 Mar. 31.) Moreover, the dietary supplement form of squalamine is not pharmaceutical grade squalamine, which requires significantly greater manufacturing efforts.

By 2006, over 300 patients had received squalamine in doses ranging from 6-700 mg/m2/day by iv administration, in three Phase I and nine Phase II studies (Hao et al., "A Phase I and pharmacokinetic study of squalamine, an aminosterol angiogenesis inhibitor," Clin Cancer Res 9, 2465-71 (2003); Herbst et al., "A phase I/IIA trial of continuous five-day infusion of squalamine lactate (MSI-1256F) plus carboplatin and paclitaxel in patients with advanced non-small cell lung cancer," Clin Cancer Res 9, 4108-15 (2003); Bhargava et al., "A phase I and pharmacokinetic study of squalamine, a novel antiangiogenic agent, in patients with advanced cancers," Clin Cancer Res 7, 3912-9 (2001); and Connolly et al., "Squalamine lactate for exudative age-related macular degeneration," Ophthalmol Clin North Am 19, 381-91, vi (2006). The studies showed that the compound exhibited an acceptable safety profile and evidence of efficacy in these early trials. For example, in the context of recommending the study of squalamine for treating certain cancers, Bhargava et al. (2001) evaluated the maximum tolerated dose (MTD), dose-limiting toxicity (DLT) and pharmacokinetics of squalamine lactate when given as a 120-h continuous i.v. infusion every two weeks. The reference concludes that the best tolerated dose rate of squalamine lactate when administered as a 120-h continuous i.v. infusion was 192 mg/m(2)/day; however, patients without prior exposure to squalamine appeared to tolerate a dose rate of 384 mg/m(2)/day without DLT. In 2006 development of squalamine was halted for economic/strategic reasons by Genaera, and has remained in a dormant stage since.

2. Toxicity of Current Squalamine and Aminosterol 1436 Formulations

Squalamine and Aminosterol 1436 are fundamentally detergents and can as a consequence disrupt the membranes of normal healthy cells (Moore, Wehrli et al. 1993). This property impacts on the utility of squalamine and Aminosterol 1436. Squalamine and related aminosterols are generally administered at daily doses of between 25-700 mg to a human subject (Bhargava, Marshall et al. 2001; Hao, Hammond et al. 2003; Herbst, Hammond et al. 2003; U.S. Pat. No. 6,962,909; Connolly, Desai et al. 2006). When solutions of squalamine or related aminosterols are administered to animals or humans, the concentrations of the active compound must be adjusted to minimize the damaging effects of the aminosterol on the tissues that will experience the initially high concentrations generally administered. For example, Hao et al. (2003) describes toxicities associated with escalating dosages of squalamine. Hepatotoxicity, characterized by brief, asymptomatic elevations in transaminases and hyperbilirubinemia, was the principal dose-limiting toxicity of squalamine. At 700 mg/m(2)/day, two of three patients developed grade 4 hyperbilirubinemia, which precluded further dose escalation. At 500 mg/m(2)/day, one of seven patients experienced dose-limiting grade 4 hyperbilirubinemia and grade 3 neurosensory changes.

Typically, squalamine or Aminosterol 1436 is administered intravenously at concentrations no greater than 1 mg/ml (Herbst, Hammond et al. 2003), (Hao, Hammond et al. 2003; US2007/10504A1 2007), (Connolly, Desai et al. 2006). Higher concentrations cause vascular inflammation due to damage to the endothelial lining of the veins into which the compound is administered. Indeed, the intravenous administration of squalamine lactate to human subjects via peripheral vein at a concentration of 1 mg/ml was associated with infusion site tissue damage, requiring the use of a more dilute solution in subsequent studies (0.25 mg/ml). (Connolly, Desai et al. 2006). Furthermore, administration of either squalamine or Aminosterol 1436 via subcutaneous or intramuscular routes would require use of significantly higher concentrations of drug to deliver the daily dose (between 25-700 mg) in a volume appropriate for these modes of local administration (1-5 ml per dosing, or between 25 mg/ml and 140 mg/ml). Because of the local tissue destruction that would be caused by the administration of these concentrations of drug, subcutaneous or intramuscular dosing of squalamine and related aminosterols to date has not been possible.

There is a need in the art for new formulations of squalamine and squalamine derivatives which that can be administered without causing local tissue damage. The present invention addresses the problem by providing new formulations of squalamine and squalamine derivatives, such as Aminosterol 1436.

SUMMARY OF THE INVENTION

The present invention relates to compositions comprising at least one salt of an aminosterol, such as squalamine, in which the salt is an inorganic phosphate, polyphosphate, or an organic phosphate monoester. The compositions, when administered in vivo, reduce the local membrane damaging properties of squalamine and other aminosterols when administered in doses required to achieve therapeutic or disease preventative benefits. The compositions of the invention can comprise one or more pharmaceutically acceptable excipients.

In various embodiments of the invention, the aminosterol is administered as a weakly water soluble salt of inorganic phosphate to an animal or human. The aminosterol can be administered as a weakly water soluble salt of inorganic pyrophosphate to an animal or human. In yet another embodiment, the aminosterol can be administered as a weakly water soluble salt of an inorganic polyphosphate, where the number of phosphates can range from 3 (tripolyphosphate) to several hundred. In another embodiment, the aminosterol can be administered as a weakly water soluble salt of an organic phosphate, including glycerol 2 phosphates, or any organic phosphate that can form a weakly water soluble salt with an aminosterol.

In one embodiment of the invention, the compositions of the invention comprising at least one poorly soluble phosphate salt of an aminosterol such as squalamine or a derivative thereof can be administered to achieve a therapeutic benefit, by both reducing the free concentration of the aminosterol liberated by the dissolving suspension, and by slowing down the rate of entry of the administered dose of the aminosterol as a result of the slow rate of dissolution of the suspension, creating a sustained release effect.

In another embodiment, the phosphate salt of an aminosterol such as squalamine or a derivative thereof can be produced as a salt form, purified, and subsequently administered as a suspension. In another embodiment, a suspension can be created from a solution of a soluble salt of an aminosterol such as squalamine or a derivative thereof by addition of sufficient phosphate to fully titrate the aminosterol. In another embodiment the phosphate can be a polyphosphate, such as pyrophosphate. In another embodiment, the chain of phosphates can be three or greater.

The aminosterol in the compositions of the invention can be squalamine, a squalamine isomer, or a derivative of squalamine. In addition, the aminosterol can be Aminosterol 1436. In yet another embodiment, any sterol having an attached polyamine, such that the molecule has a net positive charge of at least +1 created by the polyamine.

In another embodiment, the aminosterol has the chemical structure of Formula I:

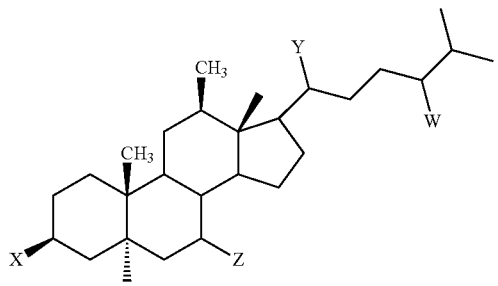

wherein,
W is 24S—OSO$_3$ or 24R—OSO$_3$;
X is 3β-H$_2$N—(CH$_2$)$_4$—NH—(CH$_2$)$_3$—NH— or 3α-H$_2$N—(CH$_2$)$_4$—NH—(CH$_2$)$_3$—NH—;
Y is 20R—CH$_3$; and
Z is 7α or 7β—OH The aminosterol present in the composition of the invention can also be a derivative of squalamine modified through medical chemistry to improve biodistribution, ease of administration, metabolic stability, or any combination thereof. In another embodiment, the squalamine or aminosterol is modified to include one or more of the following: (1) substitutions of the sulfate by a sulfonate, phosphate, carboxylate, or other anionic moiety chosen to circumvent metabolic removal of the sulfate moiety and oxidation of the cholesterol side chain; (2) replacement of a hydroxyl group by a non-metabolizable polar substituent, such as a fluorine atom, to prevent its metabolic oxidation or conjugation; and (3) substitution of various ring hydrogen atoms to prevent oxidative or reductive metabolism of the steroid ring system.

The invention also encompasses compositions comprising at least one aminosterol, such as squalamine, a squalamine derivative, a squalamine isomer or prodrug, or a pharmaceutically equivalent salt thereof, further in combination with at least one non-aminosterol active agent. For example, the compositions of the invention when used for treating viral infections can further comprise at least one antiviral agent, and/or at least one antiviral immunological adjuvant. Examples of antiviral immunological adjuvants include, but are not limited to corticosteroids, alpha-interferon, etc.

In yet another embodiment of the invention, the composition can further comprise at least one antigen capable of eliciting an immune response. For example, the antigen can be a viral or prion antigen.

The aminosterol compositions of the invention can be used to treat any indication known to be amenable to treatment with an aminosterol. The aminosterol compositions of the invention can be used to treat, for example, (1) antimicrobial infections, including treating Gram-negative and Gram-positive bacterial infections, fungal infections, and protozoan infections; (2) disease states known to be associated with pathological neovascularization, such as cancer, due to squalamine's anti-angiogenic properties; (3) vascular disorders of the eye, including macular degeneration, such as age-related macular degeneration, retinopathy of prematurity, corneal neovascularization, diabetic retinopathy; (4) weight loss or weight management, dose-dependent weight loss; (5) viral infections; (6) diseases, including viral infections, where sodium-hydrogen exchanger ("NHE-3") plays a critical role, and where its inhibition (by squalamine) could be effected; and (7) treatment of fibrodysplasia ossificans progressiva, a rare disease where connective tissue will ossify when damaged.

In certain embodiments of the invention, the methods comprise administering an aminosterol, such as squalamine or a derivative thereof, at an effective daily dosing amount of about 0.1 to 20 mg/kg body weight. In other embodiments, the effective amount is administered in a regimen that achieves and maintains a tissue concentration of the aminosterol, such as squalamine, in body organs and tissues of between about 0.1-200 µg/gram (tissue wet weight).

The composition can be administered via any pharmaceutically acceptable method, including but not limited to intravenously, subcutaneously, intramuscularly, topically, orally, or by inhalation.

For treating viral infections, in one embodiment of the invention (a) the composition does not demonstrate an altered IC$_{50}$ or IC$_{90}$ (drug concentration required to inhibit viral growth by 50% or 90% respectively) over time; (b) the composition demonstrates an IC$_{50}$ or IC$_{90}$ which does not increase by more than 0%, 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, or 30% over time; (c) the composition demonstrates an IC$_{50}$ or IC$_{90}$ which does not increase by an amount described in (b) over a time period selected from the group consisting of 1 week, 2 weeks, 3 weeks, 4 weeks, 1 month, 1.5 months, 2 months, 2.5 months, 3 months, 3.5 months, 4 months, 4.5 months, 5 months, 5.5 months, 6 months, 6.5 months, 7 months, 7.5 months, 8 months, 8.5 months, 9 months, 9.5 months, 10 months, 10.5 months, 11 months, 11.5 months, 12 months, 1 year, 1.5 years, 2 years, 2.5 years, 3 years, 3.5 years, 4 years, 4.5 years, and 5 years; or (d) any combination thereof.

The methods of the invention can further comprise administering the aminosterol, such as squalamine or derivative thereof, in combination with at least one additional active agent to achieve either an additive or synergistic antiviral effect. The additional active agent can be administered concomitantly, as an admixture, separately and simultaneously or concurrently, or separately and sequentially. For example, for compositions used to treat viral infections, the additional active agent can be: (a) an antiretroviral agent; (b) nucleoside or nucleotide reverse transcriptase inhibitors (NRTIs); (c) non-nucleoside reverse transcriptase inhibitors (NNRTIs); (d) nucleotide or nucleoside analogues; (e) protease inhibitors (PIs); (f) drugs based on "antisense" molecules; (g) ribozyme antivirals; (h) assembly inhibitors; (i) release phase inhibitors; (j) drugs which stimulate the immune system, such as interferons and synthetic antibodies; (k) fusion inhibitors/gp41 binders; (l) fusion inhibitors/chemokine receptor antagonists; (m) integrase inhibitors; (n) hydroxyurea-like compounds; (o) inhibitors of viral integrase; (p) inhibitors of viral genome nuclear translocation; (q) inhibitors of HIV entry; (r) nucleocapsid zinc finger inhibitors; (s) targets of HIV Tat and Rev; (t) pharmacoenhancers; (u) cytokines; (v) lymphokines; (w) an anti-inflammatory agent; or (x) any combination thereof.

Both the foregoing summary of the invention and the following brief description of the drawings and the detailed description of the invention are exemplary and explanatory and are intended to provide further details of the invention as claimed. Other objects, advantages, and novel features will be readily apparent to those skilled in the art from the following detailed description of the invention.

BRIEF DESCRIPTION OF THE DRAWINGS

The patent or application file contains at least one or more drawings executed in color. Copies of this patent or patent application publication with color drawing(s) will be provided by the Office upon request and payment of necessary fee.

FIG. 3: Shows a picture of a cell before (FIG. 3A) and after (FIG. 3B) exposure to squalamine. FIG. 3A shows the net negative charge at the cell surface (i.e., green circle) and FIG. 3B shows the change in cell structure following exposure to squalamine. Specifically, squalamine integrates into the cellular membrane, profoundly altering the overall charge of that membrane, and causing displacement into the cellular cytoplasm of key proteins bound to the membrane through electrostatic interactions' and required for actin remodeling to occur.

FIG. 7: Shows the results of an in vivo test to determine the effectiveness of squalamine against Eastern Equine Encephalitis virus in Syrian hamsters. Squalamine administered at 10 mg/kg/day, s.c., formulated as the phosphate suspension, is shown to increase survival, compared with a vehicle control.

DETAILED DESCRIPTION OF THE INVENTION

Figure 1:
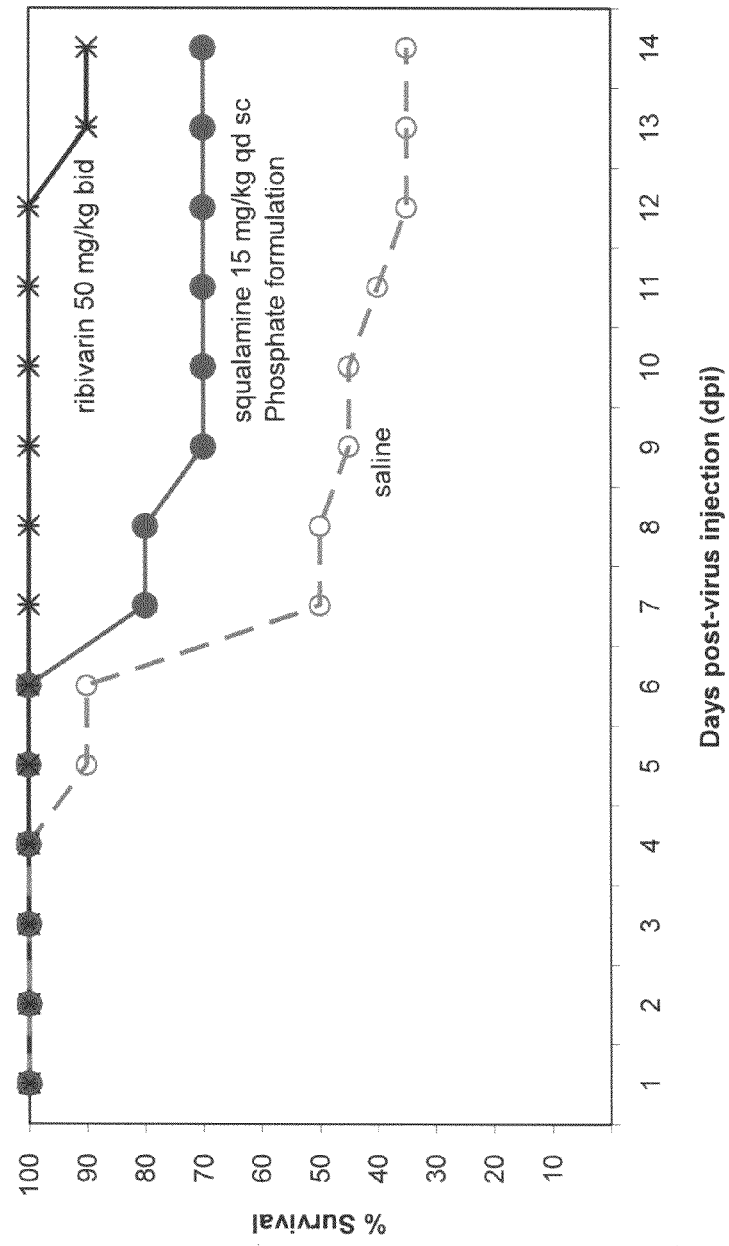
FIG. 1: Shows the percent survival as compared to days post infection (dpi) for three groups of hamsters: (1) Group I, administered squalamine phosphate suspension; (2) Group 2, administered ribavirin, which is the conventional treatment for yellow fever, and (3) Group 3, administered saline as a placebo. Animals were injected with Jimenez, a hamster adapted yellow fever virus strain. Animals receiving squalamine phosphate achieved about 70% survival by day 12 as compared to 35% for the placebo Group.

The present invention relates to aminosterol phosphate compositions, such as compositions of squalamine or derivatives thereof, which produce a reduction in local tissue damage present upon injectable (e.g., IM, SC or IV) administration of prior art aminosterol compositions. In the compositions of the invention, the aminosterol, such as squalamine or a derivative thereof, is formulated as a phosphate salt. Unlike squalamine, which is has a solubility in water exceeding 100 mg/ml, the solubility of squalamine phosphate salts in water is over 1000 fold lower, e.g., about 40 µg/ml, and about 1 µg/ml at plasma (and tissue) phosphate concentrations.

The compositions of the invention can also provide a controlled release of the aminosterol. For example, injection of 1 ml of a solution of squalamine lactate at 1 mg/ml (the commonly used salt) will expose tissues in the micro-environment of the administered dose to instantaneous squalamine concentrations of 1 mg/ml, which will gradually decrease as the compound diffuses from the site into either local tissues or into the vascular system. From the literature, concentrations of squalamine in excess of 100 μg/ml damage tissue and cellular membranes by non-specific detergent like effects, with the effect growing more intense as the concentration rises (Moore, Wehrli et al. 1993). In contrast, injection of 1 mg of a suspension of squalamine phosphate at a concentration of 1 mg/ml, will expose local tissues to a steady state concentration of squalamine no greater than 1 μg/ml, a concentration below that which causes non-specific membrane disruption. Because of the weakly soluble nature of the squalamine phosphate salt, the free concentration of squalamine in the micro-environment of the suspension is independent of the amount introduced into the site. Hence the aminosterol phosphate compositions of the invention provide a means of administering an aminosterol, such as squalamine, in a slowly releasing format that naturally controls free concentrations of the aminosterol, based solely on the solubility of squalamine phosphate in the environment of the dissolving suspension.

I. Definitions

The following definitions are provided to facilitate understanding of certain terms used throughout this specification.

As used herein, "therapeutic activity" or "activity" may refer to an activity whose effect is consistent with a desirable therapeutic outcome in humans, or to desired effects in non-human mammals or in other species or organisms. Therapeutic activity may be measured in vivo or in vitro. For example, a desirable effect may be assayed in cell culture.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, the phrase "therapeutically effective amount" shall mean the drug dosage that provides the specific pharmacological response for which the drug is administered in a significant number of subjects in need of such treatment. It is emphasized that a therapeutically effective amount of a drug that is administered to a particular subject in a particular instance will not always be effective in treating the conditions/diseases described herein, even though such dosage is deemed to be a therapeutically effective amount by those of skill in the art.

II. Aminosterols Useful in the Compositions of the Invention

This compositions of the invention comprise at least one aminosterol. Specifically, the compositions of the invention comprise: (a) at least one pharmaceutical grade aminosterol; and (b) at least one phosphate selected from the group consisting of an inorganic phosphate, an inorganic pyrophosphate, and an organic phosphate, wherein the aminosterol is formulated as a weakly water soluble salt of the phosphate. In one embodiment of the invention, the phosphate is an inorganic polyphosphate, and the number of phosphates can range from 3 (tripolyphosphate) to 400. In another embodiment, the phosphate is an organic phosphate which comprises glycerol 2 phosphates. In yet another embodiment, the aminosterol is selected from the group consisting of: (a) squalamine or a pharmaceutically acceptable salt or derivative thereof; (b) a squalamine isomer; (c) Aminosterol 1436; (d) an aminosterol comprising a sterol nucleus and a polyamine, attached at any position on the sterol, such that the molecule exhibits a net charge of at least +1, the charge being contributed by the polyamine; (e) an aminosterol which is a derivative of squalamine modified through medical chemistry to improve biodistribution, ease of administration, metabolic stability, or any combination thereof; (f) an aminosterol modified to include one or more of the following: (1) substitutions of the sulfate by a sulfonate, phosphate, carboxylate, or other anionic moiety chosen to circumvent metabolic removal of the sulfate moiety and oxidation of the cholesterol side chain; (2) replacement of a hydroxyl group by a non-metabolizable polar substituent, such as a fluorine atom, to prevent its metabolic oxidation or conjugation; and (3) substitution of various ring hydrogen atoms to prevent oxidative or reductive metabolism of the steroid ring system; (g) an aminosterol that can inhibit the formation of actin stress fibers in endothelial cells stimulated by a ligand known to induce stress fiber formation, having the chemical structure of Formula I:

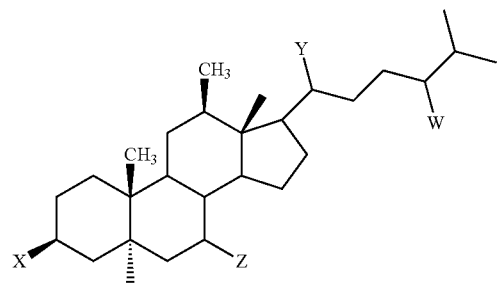

wherein,

W is 24S—OSO$_3$ or 24R—OSO$_3$;

X is 3β-H$_2$N—(CH$_2$)$_4$—NH—(CH$_2$)$_3$—NH— or 3α-H$_2$N—(CH$_2$)$_4$—NH—(CH$_2$)$_3$—NH—;

Y is 20R—CH$_3$; and

Z is 7α or 7β-OH; or (h) any combination thereof. As used herein, the term "aminosterol" is intended to encompass squalamine and derivatives thereof as described herein.

U.S. Pat. No. 6,962,909, for "Treatment of neovascularization disorders with squalamine" to Zasloff et al., discloses various aminosterols, the disclosure of which is specifically incorporated by reference. Any aminosterol known in the art, including those described in U.S. Pat. No. 6,962,909, can be used in this invention, as long as the aminosterol carries a net positive charge of at least +1 created by a polyamine moiety.

In one embodiment, the invention can be applied to a formulation of Aminosterol 1436 (Zasloff, Williams et al. 2001) as an insoluble salt of phosphate, polyphosphate, or an organic phosphate ester. In another embodiment, the aminosterol can be composed of a sterol nucleus to which a polyamine is chemically linked, displaying a net positive charge of at least +1. The invention can be embodied in a formulation comprising a suspension or as a tablet for oral administration. As an oral formulation, squalamine sulfate would slowly dissolve in the gastrointestinal tract, and not subject the lining of the intestine to high local concentrations that would otherwise irritate or damage the organ. Similarly, delivery via inhalation or nebularization would provide similar benefits. Fine particles would gradually dissolve in the airway, releasing squalamine into the lungs at non-toxic local concentrations.

An example of an aminosterol useful in the compositions of the invention includes squalamine. A variant or derivative of squalamine useful in the compositions of the invention may have one or more chemical modification which do not modify the therapeutic characteristics of squalamine. A "variant" or "derivative" of squalamine is a molecule in which modifications well known in the art of medicinal chemistry to "mimic" the original spatial and charge characteristics of a portion of the original structure have been introduced to improve the therapeutic characteristics of squalamine. In general, such modifications are introduced to influence metabolism and biodistribution. Examples of such variants or derivatives include, but are not limited to, (1) substitutions of the sulfate by a sulfonate, phosphate, carboxylate, or other anionic moiety chosen to circumvent metabolic removal of the sulfate moiety and oxidation of the cholesterol side chain; (2) replacement of an hydroxyl group by a non-metabolizable polar substituent, such as a fluorine atom, to prevent its metabolic oxidation or conjugation; and (3) substitution of various ring hydrogen atoms to prevent oxidative or reductive metabolism of the steroid ring system. As used herein, the term "squalamine" is intended to encompass squalamine and variants or derivatives thereof.

III. Striking insolubility of squalamine in the presence of inorganic phosphate and polyphosphate, but not in other common inorganic anions The solubility of various squalamine salts was examined to establish a salt form that was partially soluble in water, as described in Examples 1-3, below. These examples also determined whether an organic phosphate ester could complex with squalamine to generate a weakly soluble salt. Certain organic phosphate esters, such as glycerol-2-phosphate appear to form weakly soluble salts with squalamine, while others such as Glucose-6-phosphate do not. This difference is likely due to the degree of steric hindrance imposed by the organic moiety on electrostatic interactions between the cationic amino groups of the polyamine tail of squalamine and the anionic oxygens of the phosphate. The results of Example 1 presented below showed that the insolubility of squalamine in the presence of phosphate, pyrophosphate and polyphosphate is not observed with other common anions. ("Turbidity" in Table 1 corresponds to insolubility, as insolubility of the salt form was scored by the change in the solution from clear/transparent to turbid/cloudy.)

TABLE 1

| Salt | Turbidity |
| --- | --- |
| Sodium phosphate, pH 7.4 | Yes |
| Potassium phosphate, pH 7.4 | Yes |
| Magnesium phosphate, pH 7.4 | Yes |
| Sodium pyrophosphate | Yes |
| Sodium triphosphate | Yes |
| Sodium acetate | No |
| Sodium chloride | No |
| Sodium lactate | No |
| Sodium gluconate | No |
| Sodium sulfate | No |
| Sodium pyruvate | No |
| Sodium citrate | No |
| Sodium mesylate | No |
| Sodium trifluoracetate | No |
| Sodium carbonate | No |
| Sodium fluoride | No |
| Sodium iodate | No |
| Sodium nitrate | No |
| Glucose 6-phosphate | No |
| Glycerol 2-phosphate | Yes |

The results of examples 2 and 3 below show that the weakly soluble salt between phosphate and squalamine is a 1:1 complex between the phosphate anion and the squalamine molecule (Example 2), and that the weakly soluble salt between pyrophosphate and squalamine is a 1:2 complex between the pyrophosphate anion and two squalamine molecules.

IV. Particle size of the squalamine phosphate suspension

The compositions of the invention can also be used to control the rate of release of an aminosterol, such as squalamine, from its site of administration into the bloodstream ("sustained release"). It is well known in the art of drug formulation that depot administration of a poorly soluble suspension of drug exhibits a more sustained release of a drug into the blood stream than does the administration of a solution of that drug delivered to the same anatomic location (i.e., a subcutaneous or intramuscular site). The rate of dissolution of the particles of drug that comprise the suspension is profoundly influenced by the molecular structure and physical form (particle size, crystallinity, etc) of the drug particles. In the present invention, a given weight of an aminosterol phosphate, such as squalamine phosphate, dispersed into smaller particles will dissolve and hence distribute more rapidly than a dispersion of larger particles. The difference in dispersal time reflects the relationship between total particle surface area and particle size: the smaller the particle size the greater the surface area a given weight of an aminosterol phosphate, such as squalamine phosphate. In addition, the density of the particle (reflecting its molecular structure) can be modified to alter its dissolution properties. Thus, highly organized dense crystalline particles would be expected to dissolve more slowly than amorphous less dense forms of the phosphate salt, under identical conditions of solubilization.

The size of the particles of squalamine phosphate used for dose administration can be controlled by a variety of methods known in the field of formulation science. For example, an aminosterol phosphate powder, such as squalamine powder, can be milled to a specific mean particle size. Alternatively, a suspension of an aminosterol phosphate, such as squalamine phosphate, with a specific distribution can be generated in situ by addition of a phosphate solution to a soluble solution of an aminosterol salt (e.g., a squalamine salt). In general, particle size can be controlled by varying the molar ratio of phosphate relative to the aminosterol phosphate (e.g., squalamine) present in solution; varying the temperature under which the phosphate salt form is being prepared; altering the viscosity of solution through addition of various carbohydrates in various concentrations; and through physical agitation (mechanical or sonication) during or after preparation of the suspension.

The molecular structure of the particle can be easily controlled, for example, by adjusting the relative molar ratios of phosphate to squalamine, as described in Examples 7 and 8, creating particles of either amorphous or crystalline structure.

V. Composition Components

A. Pharmaceutical Carriers

While it is possible for an aminosterol phosphate composition to be administered alone, it is preferable to present it as a pharmaceutical formulation, together with one or more acceptable carriers. The carrier(s) must be "acceptable" in the sense of being compatible with the aminosterol (e.g., squalamine or a derivative thereof) and not deleterious to the recipients thereof. Typically, the carriers will be water or saline which will be sterile and pyrogen free. Squalamine or a derivative thereof is particularly well suited to formulation in aqueous carriers such as sterile pyrogen free water, saline or other isotonic solutions because of their extended shelf-life in solution. For instance, pharmaceutical compositions of the invention may be formulated well in advance in aqueous form, for instance, weeks or months or longer time periods before being dispensed.

Generally, the formulations are prepared by contacting the aminosterol, e.g., squalamine or a derivative thereof, uniformly and intimately with liquid carriers or finely divided solid carriers or both. Then, if necessary, the product is shaped into the desired formulation. Preferably, the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably comprises minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as gelatin, serum albumin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

In instances where aerosol administration is appropriate, the aminosterol, e.g., squalamine or a derivative thereof, can be formulated as aerosols using standard procedures. The term "aerosol" includes any gas-borne suspended phase of an aminosterol (e.g., squalamine or a derivative thereof) which is capable of being inhaled into the bronchioles or nasal passages, and includes dry powder and aqueous aerosol, and pulmonary and nasal aerosols. Specifically, aerosol includes a gas-born suspension of droplets of an aminosterol, as may be produced in a metered dose inhaler or nebulizer, or in a mist sprayer. Aerosol also includes a dry powder composition of a composition of the invention suspended in air or other carrier gas, which may be delivered by insufflation from an inhaler device, for example. See Ganderton & Jones, *Drug Delivery to the Respiratory Tract* (Ellis Horwood, 1987); Gonda, *Critical Reviews in therapeutic Drug Carrier Systems*, 6:273-313 (1990); and Raeburn et al., *Pharmacol. Toxicol. Methods*, 27:143-159 (1992).

B. Dosage Forms

The formulations may conveniently be presented in unit dosage form and may be prepared by any of the methods well known in the art of pharmacy. Any pharmaceutically acceptable dosage form may be employed in the methods of the invention. For example, the composition can be formulated: (a) for administration selected from the group consisting of oral,-pulmonary, rectal, colonic, parenteral, intracisternal, intravaginal, intraperitoneal, intravenous, subcutaneous, intramuscular, nebulization, inhalation, ocular, otic, local, buccal, nasal, and topical administration; (b) into a dosage form selected from the group consisting of liquid dispersions, gels, aerosols, ointments, creams, lyophilized formulations, tablets, capsules; (c) into a dosage form selected from the group consisting of controlled release formulations, fast melt formulations, delayed release formulations, extended release formulations, pulsatile release formulations, and mixed immediate release and controlled release formulations; or (d) any combination of (a), (b), and (c).

An exemplary dosage form is an orally administered dosage form, such as a tablet or capsule. Such methods include the step of bringing into association the aminosterol (e.g., squalamine or a derivative thereof) with the carrier that constitutes one or more accessory ingredients. In general, the formulations are prepared by uniformly and intimately bringing into association the active ingredient with liquid carriers or finely divided solid carriers or both, and then, if necessary, shaping the product.

1. Exemplary Dosage Forms

Formulations suitable for parenteral administration include aqueous and non-aqueous sterile injection solutions which may contain anti-oxidants, buffers, bacteriostats and solutes which render the formulation appropriate for the intended recipient; and aqueous and non-aqueous sterile suspensions which may include suspending agents and thickening agents. The formulations may be presented in unit-dose or multi-dose containers, for example sealed ampules, vials or syringes, and may be stored in a freeze-dried (Lyophilised) condition requiring only the addition of the sterile liquid carrier, for example water for injections, immediately prior to use. Extemporaneous injection solutions and suspensions may be prepared from sterile powders.

Formulations or compositions of the invention may be packaged together with, or included in a kit with, instructions or a package insert. For instance, such instructions or package inserts may address recommended storage conditions, such as time, temperature and light, taking into account the shelf-life of the aminosterol (e.g., squalamine or a derivative thereof). Such instructions or package inserts may also address the particular advantages of the aminosterol (e.g., squalamine or a derivative thereof), such as the ease of storage for formulations that may require use in the field, outside of controlled hospital, clinic or office conditions.

The aminosterol (e.g., squalamine or a derivative thereof) composition can also be included in nutraceuticals. For instance, the aminosterol (e.g., squalamine or a derivative thereof) composition may be administered in natural products, including milk or milk product obtained from a transgenic mammal which expresses alpha-fetoprotein fusion protein. Such compositions can also include plant or plant products obtained from a transgenic plant which expresses the aminosterol. The aminosterol (e.g., squalamine or a derivative thereof) can also be provided in powder or tablet form, with or without other known additives, carriers, fillers and diluents. Exemplary nutraceuticals are described in Scott Hegenhart, *Food Product Design*, December 1993.

The aminosterol (e.g., squalamine or a derivative thereof) composition will be formulated and dosed in a fashion consistent with good medical practice, taking into account the clinical condition of the individual patient (especially the side effects of treatment with the aminosterol alone), the site of delivery, the method of administration, the scheduling of administration, and other factors known to practitioners. The "effective amount" for purposes herein is thus determined by such considerations.

As a general proposition, the total pharmaceutically effective amount of the aminosterol (e.g., squalamine or a derivative thereof) administered parenterally per dose will be in the range of about 0.1 mg/kg/day to 20 mg/kg/day of patient body weight, although, as noted above, this will be subject to therapeutic discretion. An intravenous bag solution may also be employed. The length of treatment needed to observe changes and the interval following treatment for responses to occur appears to vary depending on the desired effect.

"Pharmaceutically acceptable carrier" refers to a non-toxic solid, semisolid or liquid filler, diluent, encapsulating material or formulation auxiliary of any. The term "parenteral" as used herein refers to modes of administration which include intravenous, intramuscular, intraperitoneal, intrasternal, subcutaneous, transdermal, and intraarticular injection and infusion.

The aminosterol (e.g., squalamine or a derivative thereof) is also suitably administered by sustained-release systems. Examples of sustained-release aminosterol (e.g., squalamine or a derivative thereof) compositions are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion. Additional examples of sustained-release compositions include suitable polymeric materials (such as, for example, semi-permeable polymer matrices in the form of shaped articles, e.g., films, or mirocapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman et al., *Biopolymers*, 22:547-556 (1983)), poly (2-hydroxyethyl methacrylate) (Langer et al., *J. Biomed. Mater. Res.*, 15:167-277 (1981), and Langer, *Chem. Tech.*, 12:98-105 (1982)), ethylene vinyl acetate (Langer et al., Id.) or poly-D-(−)-3-hydroxybutyric acid (EP 133,988).

Sustained-release aminosterols (e.g., squalamine or a derivative thereof) also include liposomally entrapped aminosterol (see generally, Langer, *Science*, 249:1527-1533 (1990); Treat et al., in *Liposomes in the Therapy of Infectious Disease and Cancer*, Lopez-Berestein and Fidler (eds.), pp. 317-327 and 353-365 (Liss, N.Y., 1989). Liposomes comprising the aminosterol (e.g., squalamine or a derivative thereof) are prepared by methods known per se: DE 3,218,121; Epstein et al., *Proc. Natl. Acad. Sci.* (USA), 82:3688-3692 (1985); Hwang et al., *Proc. Natl. Acad. Sci.* (USA), 77:40304034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal therapeutic.

In yet an additional embodiment, the aminosterol (e.g., squalamine or a derivative thereof) is delivered by way of a pump (see Langer, supra; Sefton, *CRC Crit. Ref. Biomed. Eng.*, 14:201 (1987); Buchwald et al., *Surgery*, 88:507 (1980); Saudek et al., *N. Engl. J. Med.*, 321:574 (1989)).

Other controlled release systems are discussed in the review by Langer (*Science* 249:1527-1533 (1990)).

For parenteral administration, in one embodiment, the aminosterol (e.g., squalamine or a derivative thereof) composition is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to the therapeutic.

Any pharmaceutical used for therapeutic administration can be sterile. Sterility is readily accomplished by filtration through sterile filtration membranes (e.g., 0.2 micron membranes). The aminosterol (e.g., squalamine or a derivative thereof) generally is placed into a container having a sterile access port, for example, an intravenous solution bag or vial having a stopper pierceable by a hypodermic injection needle.

The aminosterol (e.g., squalamine or a derivative thereof) ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous squalamine or a derivative thereof solution, and the resulting mixture is lyophilized. The infusion solution is prepared by reconstituting the lyophilized squalamine or a derivative thereof using bacteriostatic Water-for-Injection. In this embodiment, for example, a measured amount of a solution of a phosphate salt can then be added to the aqueous solution of squalamine or a derivative thereof to create the phosphate formulation disclosed herein.

The invention also provides a pharmaceutical pack or kit comprising one or more containers filled with one or more of the ingredients of the aminosterol (e.g., squalamine or a derivative thereof) composition including containers filled with an appropriate amount of a phosphate, either as a powder, to be dissolved, or as a sterile solution. Associated with such container(s) can be a notice in the form prescribed by a governmental agency regulating the manufacture, use or sale of pharmaceuticals or biological products, which notice reflects approval by the agency of manufacture, use or sale for human administration. In addition, the aminosterol (e.g., squalamine or a derivative thereof) may be employed in conjunction with other therapeutic compounds.

2. Other Pharmaceutical Excipients

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art.

Examples of filling agents include lactose monohydrate, lactose anhydrous, and various starches; examples of binding agents include various celluloses and cross-linked polyvinylpyrrolidone, microcrystalline cellulose, such as AVICEL® PH 101 (trade name needed) and AVICEL® PH 102 (trade name needed), microcrystalline cellulose, and silicified microcrystalline cellulose (ProSolv SMCC™)

Suitable lubricants, including agents that act on the flowability of the powder to be compressed, may include colloidal silicon dioxide, such as AEROSIL® 200 (trade name needed), talc, stearic acid, magnesium stearate, calcium stearate, and silica gel.

Examples of sweeteners may include any natural or artificial sweetener, such as sucrose, xylitol, sodium saccharin, cyclamate, aspartame, and acesulfame. Examples of flavoring agents are MAGNASWEET® (trademark of MAFCO) (trade name needed), bubble gum flavor, and fruit flavors, and the like.

Examples of preservatives include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Aviccl® AVICEL® PH101 (trade name needed), and AVICEL® PH102 (trade name needed); lactose such as lactose monohydrate, lactose anhydrous, and PHARMATOSE® DCL21 (trade name needed); dibasic calcium phosphate such as EMCOMPRESS® (trade name needed); mannitol; starch; sorbitol; sucrose; andglucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents include effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

3. Dosages

Examples of dosages of aminosterols such as squalamine tolerated by humans are well known in the art. For example, Hao et al., (2003). "A Phase I and pharmacokinetic study of squalamine, an aminosterol angiogenesis inhibitor." Clin Cancer Res 9(7): 2465-71, describes exemplary dosages for a 5-day continuous i.v. infusion every 3 weeks for treating advanced solid malignancies. Dose levels ranging from 6 to 700 mg/m(2)/day. Hepatotoxicity, characterized by brief, asymptomatic elevations in transaminases and hyperbilirubinemia, was the principal dose-limiting toxicity of squalamine. At 700 mg/m(2)/day, two of three patients developed grade 4 hyperbilirubinemia, which precluded further dose escalation. At 500 mg/m(2)/day, one of seven patients experienced dose-limiting grade 4 hyperbilirubinemia and grade 3 neurosensory changes, which resolved soon after treatment. Squalamine pharmacokinetics were dose-proportional. At 500 mg/m(2)/day, the mean (percentage coefficient of variation) clearance, half-life, and volume of distribution of squalamine were 2.67 liters/h/m(2) (85%), 9.46 h (81%), and 36.84 liters/m(2) (124%), respectively, and steady-state concentrations [20.08 micro g/ml (13%)] were well above those that inhibit angiogenesis in preclinical models. The study concluded that at a dose of 500 mg/m(2)/day, squalamine is well tolerated.

In addition, Herbst et al., (2003). "A phase I/IIA trial of continuous five-day infusion of squalamine lactate (MSI-1256F) plus carboplatin and paclitaxel in patients with advanced non-small cell lung cancer." Clin Cancer Res 9(11): 4108-15, also describes exemplary therapeutic dosage of squalamine. This reference describes a Phase I/IIA study designed to assess the safety, clinical response, and pharmacokinetics of squalamine when administered as a 5-day continuous infusion in conjunction with standard chemotherapy every 3 weeks in patients with stage IIIB (pleural effusion) or stage IV non-small cell lung cancer. Patients with chemotherapy-naive non-small cell lung cancer were treated with escalating doses of squalamine in combination with standard doses of paclitaxel and carboplatin. Paclitaxel and carboplatin were administered on day 1, followed by squalamine as a continuous infusion on days 1-5, every 21 days. The starting dose of squalamine was 100 mg/m(2)/day and escalated to 400 mg/m(2)/day; two of three patients at 400 mg/m(2)/day had dose-limiting toxicity that included grade 3/4 arthralgia, myalgia, and neutropenia. On the basis of safety and toxicity, 300 mg/m(2)/day was selected as the Phase II dose of squalamine in this combination regimen. The combination of squalamine given continuously daily for 5 days, with paclitaxel and carboplatin given on day 1, was well tolerated.

C. Adjuvants

The aminosterol (e.g., squalamine or a derivative thereof) may be administered alone or in combination with one or more adjuvants. For example, for antiviral applications, an adjuvant is a substance that indirectly enhances the therapeutic activity of the aminosterol by stimulating the antiviral arm of the innate and/or the adaptive immune system. Adjuvants that may be administered with the aminosterol (e.g., squalamine or a derivative thereof) include, but are not limited to, cytokines and/or interleukins (such as IL2, IL3, IL4, IL5, IL6, IL7, IL8, IL-9, IL10, IL-11, IL12, IL13, IL-14, IL15, IIL16, IL-17, IL-18, IL-19, IL-20, IL-21, anti-CD40, CD40L, IFN-gamma, TNF-alpha, IL-1alpha, IL-1beta), Lipid A, including monophosphoryl lipid A, bacterial products, endotoxins, cholesterol, fatty acids, aliphatic amines, paraffinic and vegetable oils, threonyl derivative, and muramyl dipeptide, alum, alum plus deoxycholate (ImmunoAg), MTP-PE (Biocine Corp.), QS21 (Genentech, Inc.), BCG (e.g., THERACYS®), MPL and nonviable preparations of *Corynebacterium parvum*. In a specific embodiment, aminosterol (e.g., squalamine or a derivative thereof) is administered in combination with alum. In another specific embodiment, aminosterol (e.g., squalamine or a derivative thereof) is administered in combination with QS-21. Further adjuvants that may be administered with the aminosterol (e.g., squalamine or a derivative thereof) include, but are not limited to, Monophosphoryl lipid immunomodulator, AdjuVax 100a, QS-21, QS-18, CRL1005, Aluminum salts, MF-59, and Virosomal adjuvant technology.

D. Vaccines

Vaccines that may be administered with the aminosterol (e.g., squalamine or a derivative thereof) include any antigen capable of eliciting an immune response. The vaccine may be comprised of either live or inactivated virus. Exemplary vaccines include, but are not limited to, vaccines directed toward protection against MMR (measles, mumps, rubella), polio, varicella, tetanus/diptheria, hepatitis A, hepatitis B, *Haemophilus influenzae* B, whooping cough, pneumonia, influenza, Lyme's Disease, rotavirus, cholera, yellow fever, Japanese encephalitis, poliomyelitis, rabies, typhoid fever, pertussis, PA-toxin (e.g., anthrax), Human Immunodeficiency Virus (HIV-1 and HIV-2), Avian Flu antigen (e.g., H5N1; avian influenza virus A/FPV/Rostock/34 (H7N1) (FPV)), cancer, Severe Acute Respiratory Syndrome (SARS), and tuberculosis. Useful antigens include but are not limited to viral, prion, bacterial, parasitic, mycotic, etc. antigens.

Combinations may be administered either concomitantly, e.g., as an admixture, separately but simultaneously or concurrently; or sequentially. In addition, as used herein "combination administration" includes compounds which are attached to the squalamine or a derivative thereof. This also includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

E. Combination Therapy

The aminosterol phosphate compositions of the invention may be administered alone or in combination with other therapeutic agents. As noted above, the aminosterol phosphate compositions of the invention are useful in treating and/or preventing: (1) viral infections, (2) antimicrobial infections, including but not limited to Gram-negative and Gram-positive bacterial infections, fungal infections, and protozoan infections; (3) disease states known to be associated with pathological neovascularization, such as cancer, due to squalamine's anti-angiogenic properties; (4) vascular disorders of the eye, including macular degeneration, such as age-related macular degeneration, retinopathy of prematurity, corneal neovascularization, diabetic retinopathy; (5) weight loss or weight management, dose-dependent weight loss; (6) diseases, including viral infections, where sodium-hydrogen exchanger ("NHE-3") plays a critical role, and where its inhibition (by squalamine) could be effected; and (7) treatment of fibrodysplasia ossificans progressiva, a rare disease where connective tissue will ossify when damaged. Thus, any active agent known to be useful in treating these conditions can be used in conjunction with the aminosterol phosphate compositions of the invention. For example, in methods of treating a microbial infection, the aminosterol phosphate compositions of the invention can be co-administered or combined with an antibiotic. For treating a viral infection, the aminosterol phosphate compositions of the invention can be co-administered or combined with an antiviral agent, etc.

For example, the aminosterol phosphate compositions may be administered in combination compounds including but not limited to, chemotherapeutic agents, antibiotics, steroidal and non-steroidal anti-inflammatories, conventional immunotherapeutic agents, antiviral agents, and/or therapeutic treatments described below. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

1. Anti-Viral Agents

For example, aminosterol phosphate compositions of the invention can be combined with conventional antiviral therapies for treating and preventing viral infections. For example, the aminosterol phosphate compositions of the invention can be combined with any known antiviral agent.

Designing safe and effective antiviral drugs is difficult, because viruses use the host's cells to replicate. This makes it difficult to find targets for the drug that would interfere with the virus without harming the host organism's cells. Almost all anti-microbials, including anti-virals, are subject to drug resistance as the pathogens mutate over time, becoming less susceptible to the treatment. For instance, a recent study published in Nature Biotechnology emphasized the urgent need for augmentation of oseltamivir (TAMIFLU®) stockpiles with additional antiviral drugs including zanamivir (RELENZA®) based on an evaluation of the performance of these drugs in the scenario that the 2009 H1N1 'Swine Flu' neuraminidase (NA) were to acquire the TAMIFLU® resistance (His274Tyr) mutation which is currently wide-spread in seasonal H1N1 strains. Soundararajan et al., "Extrapolating from sequence—the 2009 H1N1 'swine' influenza virus". Nature Biotechnology 27 (6) (2009). Thus, there is a need for compositions, such as those described herein, which are useful in conjunction with conventional antiviral treatments.

Conventional antiviral treatments include, but are not limited to (1) Amantadine and rimantadine, which combat influenza and act on penetration/uncoating; (2) Pleconaril, which works against rhinoviruses, which cause the common cold; (3) nucleotide or nucleoside analogues, such as acyclovir, zidovudine (AZT), lamivudine; (4) drugs based on "anti-sense" molecules, such as fomivirsen; (5) ribozyme antivirals; (6) protease inhibitors; (7) assembly inhibitors, such as Rifampicin; (8) release phase inhibitors, such as zanamivir (Relenza) and oseltamivir (TAMIFLU®); (9) drugs which stimulate the immune system, such as interferons, which inhibit viral synthesis in infected cells (e.g., interferon alpha), and synthetic antibodies (A monoclonal drug is now being sold to help fight respiratory syncytial virus in babies, and antibodies purified from infected individuals are also used as a treatment for hepatitis B). Examples of antiviral drugs include, but are not limited to, Abacavir, Aciclovir, Acyclovir, Adefovir, Amantadine, Amprenavir, Arbidol, Atazanavir, Atripla, Boceprevir, Cidofovir, Combivir, Darunavir, Delavirdine, Didanosine, Docosanol, Edoxudine, Efavirenz, Emtricitabine, Enfuvirtide, Entecavir, Entry inhibitors, Famciclovir, Fixed dose combination (antiretroviral), Fomivirsen, Fosamprenavir, Foscarnet, Fosfonet, Fusion inhibitor, Ganciclovir, Ibacitabine, Immunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Molixan (NOV-205), Moroxydine, Nelfinavir, Nevirapine, Nexavir, Nucleoside analogues, Oseltamivir (TAMIFLU®), Peginterferon alfa-2a, Penciclovir, Peramivir, Pleconaril, Podophyllotoxin, Protease inhibitor (pharmacology), Raltegravir, Reverse transcriptase inhibitor, Ribavirin, Rimantadine, Ritonavir, Saquinavir, Stavudine, Synergistic enhancer (antiretroviral), Tenofovir, Tenofovir disoproxil, Tipranavir, Trifluridine, Trizivir, Tromantadine, Truvada, Valaciclovir (Valtrex), Valganciclovir, Vicriviroc, Vidarabine, Viramidine, Zalcitabine, Zanamivir (Relenza), and Zidovudine.

In certain embodiments, squalamine or a derivative thereof is administered in combination with antiretroviral agents, nucleoside/nucleotide reverse transcriptase inhibitors (NRTIs), non-nucleoside reverse transcriptase inhibitors (NNRTIs), and/or protease inhibitors (PIs). NRTIs that may be administered in combination with the squalamine or a derivative thereof, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). NNRTIs that may be administered in combination with squalamine composition, include, but are not limited to, VIRAMUNE™ (nevirapine), RESCRIPTOR™ (delavirdine), and SUSTIVA™ (efavirenz). Protease inhibitors that may be administered in combination with the squalamine or a derivative thereof include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with squalamine or a derivative thereof to treat AIDS and/or to prevent or treat HIV infection.

Additional NRTIs include LODENOSINE™ (F-ddA; an acid-stable adenosine NRTI; Triangle/Abbott; COVIRACIL™ (emtricitabine/FTC; structurally related to lamivudine (3TC) but with 3- to 10-fold greater activity in vitro; Triangle/Abbott); dOTC (BCH-10652, also structurally related to lamivudine but retains activity against a substantial proportion of lanivudine-resistant isolates; Biochem Pharma); Adefovir (refused approval for anti-HIV therapy by FDA; Gilead Sciences); PREVEON® (Adefovir Dipivoxil, the active prodrug of adefovir; its active form is PMEA-pp); TENOFOVIR™ (bis-POC PMPA, a PMPA prodrug; Gilead); DAPD/DXG (active metabolite of DAPD; Triangle/Abbott); D-D4FC (related to 3TC, with activity against AZT/3TCresistant virus); GW420867 (Glaxo Wellcome); ZIAGEN™ (abacavir/159U89; Glaxo Wellcome Inc.); CS-87 (3' azido-2',3'-dideoxyuridine; WO 99/66936); and S-acyl-2-thioethyl (SATE)-bearing prodrug forms of beta-L-FD4C and P-L-FddC (WO 98/17281).

Additional NNRTIs include COACTINON™ (Emivirine/MKC442, potent NNRTI of the HEPT class; Triangle/Abbott); CAPRAVIRINE™ (AG-1549/S-1153, a next generation NNRTI with activity against viruses containing the K103N mutation; Agouron); PNU-142721 (has 20- to 50-fold greater activity than its predecessor delavirdine and is active against K103N mutants; Pharmacia & Upjohn); DPC-961 and DPC-963 (second-generation derivatives of efavirenz, designed to be active against viruses with the K103N mutation; DuPont); GW420867X (has 25-fold greater activity than HBY097 and is active against K103N mutants; Glaxo Wellcome); CALANOLIDE A (naturally occurring agent from the latex tree; active against viruses containing either or both the Y181C and K103N mutations); and Propolis (WO 99/49830).

Additional protease inhibitors include LOPINAVIR™ (ABT378/r; Abbott Laboratories); BMS-232632 (an azapeptide; Bristol-Myres Squibb); TIPRANAVIR™ (PNU-140690, a non-peptic dihydropyrone; Pharmacia & Upjohn); PD-178390 (a nonpeptidic dihydropyrone; Parke-Davis); BMS 232632 (an azapeptide; Bristol-Myers Squibb); L-756,423 (an indinavir analog; Merck); DMP450 (a cyclic urea compound; Avid & DuPont); AG-1776 (a peptidomimetic with in vitro activity against protease inhibitor-resistant viruses; Agouron); VX-175/GW433908 (phosphate prodrug of amprenavir; Vertex & Glaxo Welcome); CGP61755 (Ciba); and AGENERASE™ (amprenavir; Glaxo Wellcome Inc.).

Additional antiretroviral agents include fusion inhibitors/gp41 binders. Fusion inhibitors/gp41 binders include T-20 (a peptide from residues 643-678 of the HIV gp41 transmembrane protein ectodomain which binds to gp41 in its resting state and prevents transformation to the fusogenic state; Trimeris) and T-1249 (a second-generation fusion inhibitor; Trimeris).

Additional antiretroviral agents include fusion inhibitors/chemokine receptor antagonists. Fusion inhibitors/chemokine receptor antagonists include CXCR4 antagonists such as AMD 3100 (a bicyclam), SDF-1 and its analogs, and ALX404C (a cationic peptide), T22 (an 18 amino acid peptide; Trimeris) and the T22 analogs T134 and T140; CCR5 antagonists such as RANTES (9-68), AOP-RANTES, NNY-RANTES, and TAK-779; and CCR5/CXCR4 antagonists such as NSC 651016 (a distamycin analog). Also included are CCR2B, CCR3, and CCR6 antagonists. Chemokine receptor agonists such as RANTES, SDF-1, MEP-1alpha, MIP-1beta, etc., may also inhibit fusion.

Additional antiretroviral agents include integrase inhibitors. Integrase inhibitors include dicaffeoylquinic (DFQA) acids; L-chicoric acid (a dicaffeoyltartaric (DCTA) acid); quinalizarin (QLC) and related anthraquinones; ZINTEVIR™ (AR 177, an oligonucleotide that probably acts at cell surface rather than being a true integrase inhibitor; Arondex); and naphthols such as those disclosed in WO 98/50347.

Additional antiretroviral agents include hydroxyurea-like compounds such as BCX-34 (a purine nucleoside phosphorylase inhibitor; Biocryst); ribonucleotide reductase inhibitors such as DIDOX™ (Molecules for Health); inosine monophosphate dehydrogenase (IMPDH) inhibitors such as VX-497 (Vertex); and mycopholic acids such as CellCept (mycophenolate mofetil; Roche).

Additional antiretroviral agents include inhibitors of viral integrase, inhibitors of viral genome nuclear translocation such as arylene bis(methylketone) compounds; inhibitors of HIV entry such as AOP-RANTES, NNY-RANTES, RANTES-IgG fusion protein, soluble complexes of RANTES and glycosaminoglycans (GAG), and AMD-3100; nucleocapsid zinc finger inhibitors such as dithiane compounds; targets of HIV Tat and Rev; and pharmacoenhancers such as ABT-378.

Other antiretroviral therapies and adjunct therapies include cytokines and lymphokines such as MIP-1alpha, MIP-1beta, SDF-1alpha, IL-2, PROLEUKIN™ (aldesleukin/L2-7001; Chiron), IL4, IL-10, IL-12, and IL-13; interferons such as IFN-alpha2a, IFN-alpha2b, or IFN-beta; antagonists of TNFs, NFkappaB, GM-CSF, M-CSF, and IL-10; agents that modulate immune activation such as cyclosporin and prednisone; vaccines such as REMUNE™ (HIV Immunogen), APL 400-003 (Apollon), recombinant gp120 and fragments, bivalent (B/E) recombinant envelope glycoprotein, rgp120CM235, MN rgp120, SF-2 rgp120, gp120/soluble CD4 complex, Delta JR-FL protein, branched synthetic peptide derived from discontinuous gp120 C3/C4 domain, fusion-competent immunogens, and Gag, Pol, Nef, and Tat vaccines; gene-based therapies such as genetic suppressor elements (GSEs; WO 98/54366), and intrakines (genetically modified CC chemokines targeted to the ER to block surface expression of newly synthesized CCR5 (Yang et al., *PNAS*, 94:11567-72 (1997); Chen et al., *Nat. Med.*, 3:1110-16 (1997)); antibodies such as the anti-CXCR4 antibody 12G5, the anti-CCR5 antibodies 2D7, 5C7, PA8, PA9, PA10, PA11, PA12, and PA14, the anti-CD4 antibodies Q4120 and RPA-T4, the anti-CCR3 antibody 7B11, the anti-gp120 antibodies 17b, 48d, 447-52D, 257-D, 268-D and 50.1, anti-Tat antibodies, anti-TNF-alpha antibodies, and monoclonal antibody 33A; aryl hydrocarbon (AH) receptor agonists and antagonists such as TCDD, 3,3',4,4',5-pentachlorobiphenyl, 3,3',4,4'-tetrachlorobiphenyl, and alpha-naphthoflavone (WO 98/30213); and antioxidants such as gamma-L-glutamyl-L-cysteine ethyl ester (gamma-GCE; WO 99/56764).

2. Anti-Inflammatory Agents

In certain embodiments, the aminosterol phosphate composition is administered alone or in combination with an anti-inflammatory agent. Anti-inflammatory agents that may be administered with the aminosterol phosphate compositions include, but are not limited to, corticosteroids (e.g. betamethasone, budesonide, cortisone, dexamethasone, hydrocortisone, methylprednisolone, prednisolone, prednisone, and triamcinolone), nonsteroidal anti-inflammatory drugs (e.g., diclofenac, diflunisal, etodolac, fenoprofen, floctafenine, flurbiprofen, ibuprofen, indomethacin, ketoprofen, meclofenamate, mefenamic acid, meloxicam, nabumetone, naproxen, oxaprozin, phenylbutazone, piroxicam, sulindac, tenoxicam, tiaprofenic acid, and tolmetin), as well as antihistamines, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

3. Antibiotic Agents

In certain embodiments, the aminosterol phosphate composition is administered alone or in combination with one or more antibiotics. Examples of such antibiotic agents include, but are not limited to, aminoglycosides, Ansamycins, Carbacephems, Carbapenems, Cephalosporins, Glycopeptides, Macrolides, Monobactams, Penicillins, Polypeptides, Polymyxin, Quinolones, Sulfonamides, Tetracyclines, and others (e.g., Arsphenamine, Chloramphenicol, Clindamycin, Lincomycin, Ethambutol, Fosfomycin, Fusidic acid, Furazolidone, Isoniazid, Linezolid, Metronidazole, Mupirocin, Nitrofurantoin, Platensimycin, Pyrazinamide, Quinupristin/Dalfopristin, Rifampicin (Rifampin in US), Thiamphenicol, Timidazole, Dapsone, and lofazimine).

Examples of these classes of antibiotics include, but are not limited to, Amikacin, Gentamicin, Kanamycin, Neomycin, Netilmicin, Streptomycin, Tobramycin, Paromomycin, Geldanamycin, Herbimycin, Loracarbef, Ertapenem, Doripenem, Imipenem/Cilastatin, Meropenem, Cefadroxil, Cefazolin, Cefalotin or Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftobiprole, Teicoplanin, Vancomycin, Azithromycin, Clarithromycin, Dirithromycin, Erythromycin, Roxithromycin, Troleandomycin, Telithromycin, Spectinomycin, Aztreonam, Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin, Ticarcillin, Bacitracin, Colistin, Polymyxin B, Ciprofloxacin, Enoxacin, Gatifloxacin, Levofloxacin, Lomefloxacin, Moxifloxacin, Norfloxacin, Ofloxacin, Trovafloxacin, Grepafloxacin, Sparfloxacin, Temafloxacin, Mafenide, Sulfonamidochrysoidine (archaic), Sulfacetamide, Sulfadiazine, Sulfamethizole, Sulfanilimide (archaic), Sulfasalazine, Sulfisoxazole, Trimethoprim, rimethoprim-Sulfamethoxazole (Co-trimoxazole) (TMP-SMX), Demeclocycline, Doxycycline, Minocycline, Oxytetracycline, and Tetracycline.

4. Antifungal Agents

In certain embodiments, the aminosterol phosphate composition is administered alone or in combination with one or more antifungal, antiyeast or antimold agents.

Exemplary active agents include, but are not limited to, (1) azoles (imidazoles), (2) antimetabolites, (3) allylamines, (4) morpholine, (5) glucan Synthesis Inhibitors (chemical family: echinocandins), (6) polyenes, (7) benoxaborales, (8) other antifungal/onychomycosis agents, and (9) new classes of antifungal/onychomycosis agents.

Examples of azoles include, but are not limited to, Bifonazole, Clotrimazole, Econazole, Miconazole, Tioconazole, Fluconazole, Itraconazole, Ketoconazole, Pramiconazole, Ravuconazole, Posaconazole, and Voriconazole. An example of an antimetabolite includes, but is not limited to, Flucytosine. Examples of allylamines include, but are not limited to, Terbinafine and Naftidine. Morpholine is also known as amorolfine. Examples of glucan Synthesis Inhibitors include, but are not limited to, Caspofungin, Micafungin, and Anidulafungin. Examples of polyenes include, but are not limited to, Amphotericin B, Nystatin, and pimaricin. An example of a benoxaborale is AN2690. Other examples of antifungal agents include, but are not limited to, griseofulvin and ciclopirox. Finally, examples of new classes of antifungal/onychomycosis agents include, but are not limited to, sodarin derivatives and nikkomycins.

5. Anticancer Agents

In certain embodiments, the aminosterol phosphate composition is administered alone or in combination with one or more anticancer agents. For example, the anticancer agent may be a nitrosourea (such as BCNU), cyclophosphamide, adriamycin, 5-fluorouracil, paclitaxel and its derivatives, cisplatin or other platinum containing cancer treating agents.

There are no limitations on the chemotherapeutic agent that can be used in this invention. Other conventional chemotherapeutic agents that can be used with the aminosterol phosphate composition of the invention include, for example, methotrexate, thiotepa, mitoxantrone, vincristine, vinblastine, etoposide, ifosfamide, bleomycin, procarbazine, chlorambucil, fludarabine, mitomycin C, vinorelbine, and gemcitabine.

The majority of chemotherapeutic drugs can be divided in to alkylating agents, antimetabolites, anthracyclines, plant alkaloids, topoisomerase inhibitors, and other antitumour agents. All of these drugs affect cell division or DNA synthesis and function in some way. Some newer agents do not directly interfere with DNA. These include monoclonal antibodies and the new tyrosine kinase inhibitors e.g. imatinib mesylate (Gleevec or Glivec), which directly targets a molecular abnormality in certain types of cancer (chronic myelogenous leukemia, gastrointestinal stromal tumors). In addition, some drugs that modulate tumor cell behaviour without directly attacking those cells may be used. Hormone treatments fall into this category.

Alkylating agents: Alkylating antineoplastic agents are so named because of their ability to add alkyl groups to many electronegative groups under conditions present in cells. Cisplatin and carboplatin, as well as oxaliplatin, are alkylating agents. Other agents are mechlorethamine, cyclophosphamide, chlorambucil, ifosfamide.

Anti-metabolites: Plant alkaloids and terpenoids are derived from plants and block cell division by preventing microtubule function. The main examples are vinca alkaloids and taxanes. Vinca alkaloids include Vincristine, Vinblastine, Vinorelbine, and Vindesine. Podophyllotoxin is used to produce two other cytostatic drugs, etoposide and teniposide. The prototype taxane is the natural product paclitaxel. Docetaxel is a semi-synthetic analogue of paclitaxel.

Topoisomerase inhibitors include camptothecins (irinotecan and topotecan, amsacrine, etoposide, etoposide phosphate, teniposide, dactinomycin, doxorubicin, epirubicin, bleomycin and others.

6. Weight Loss Agents

In certain embodiments, the aminosterol phosphate composition is administered alone or in combination with one or more appetite suppressants or weight loss agents.

VI. Methods of Using the Compositions of the Invention

The invention also provides methods of treatment and/or prevention of diseases or disorders (such as, for example, any one or more of the diseases or disorders disclosed herein) by administration to a subject of an effective amount of a aminosterol (e.g., squalamine or a derivative thereof) in a pharmaceutically acceptable carrier. The compositions of the invention can be administered using any pharmaceutically acceptable method, including but not limited to intravenous, intramuscular, subcutaneous, oral, pulmonary, nasal, and nebularization administration.

The aminosterol compositions of the invention can be used to treat any indication known to be amenable to treatment with an aminosterol. The aminosterol compositions of the invention can be used to treat, for example, (1) viral infections, (2) antimicrobial infections, including but not limited to treating and/or preventing Gram-negative and Gram-positive bacterial infections, fungal infections, and protozoan infections; (3) disease states known to be associated with pathological neovascularization, such as cancer, due to squalamine's anti-angiogenic properties; (4) vascular disorders of the eye, including macular degeneration, such as age-related macular degeneration, retinopathy of prematurity, corneal neovascularization, diabetic retinopathy; (5) weight loss or weight management, dose-dependent weight loss; (6) diseases, including viral infections, where sodium-hydrogen exchanger ("NHE-3") plays a critical role, and where its inhibition (by squalamine) could be effected; (7) treatment of fibrodysplasia ossificans progressiva, a rare disease where connective tissue will ossify when damaged; and (8) disorders of neovascularization.

A. Treating Viral Infections

The present invention is directed to methods of treating and/or preventing viral infections comprising administering a therapeutically effective amount of an aminosterol phosphate composition to a subject in need. A "subject in need" is a human or animal at risk of a viral infection, or which has contracted a viral infection. As noted above, this method encompasses using an aminosterol phosphate composition in combination with conventional antiviral treatments to treat viral infections.

The viral infection to be treated or prevented can be caused by any virus, including but not limited to, "African Swine Fever Viruses," Arbovirus, Adenoviridae, Arenaviridae, Arterivirus, Astroviridae, Baculoviridae, Bimaviridae, Birnaviridae, Bunyaviridae, Caliciviridae, Caulimoviridae, Circoviridae, Coronaviridae, Cystoviridae, Dengue, EBV, HIV, Deltaviridae, Filviridae, Filoviridae, Flaviviridae, Hepadnaviridae (Hepatitis), Herpesviridae (such as, Cytomegalovirus, Herpes Simplex, Herpes Zoster), Iridoviridae, Monon-egavirus (e.g., Paramyxoviridae, Morbillivirus, Rhabdoviridae), Myoviridae, Orthomyxoviridae (e.g., Influenza A, Influenza B, and parainfluenza), Papiloma virus, Papovaviridae, Paramyxoviridae, Prions, Parvoviridae, Phycodnaviridae, Picornaviridae (e.g. Rhinovirus, Poliovirus), Poxyiridae (such as Smallpox or Vaccinia), Potyviridae, Reoviridae (e.g., Rotavirus), Retroviridae (HTLV-I, HTLV-II, Lentivirus), Rhabdoviridae, Tectiviridae, Togaviridae (e.g., Rubivirus), or any combination thereof. In another embodiment of the invention, the viral infection is caused by a virus selected from the group consisting of herpes, pox, papilloma, corona, influenza, hepatitis, sendai, sindbis, vaccinia viruses, west nile, hanta, or viruses which cause the common cold. In another embodiment of the invention, the condition to be treated is selected from the group consisting of AIDS, viral meningitis, Dengue, EBV, hepatitis, and any combination thereof.

For example, the results of Example 14 below demonstrate the successful treatment of animals infected with Yellow Fever. These results demonstrate that squalamine can be utilized as an effective systemic antiviral therapy in already established viral infection when administered in the squalamine phosphate formulation disclosed in this application. Because of the similarity in the properties shared by the flavivirus family, in addition to Yellow Fever, squalamine could be used to treat infections caused other members of the Flaviviridae including: Dengue, Hepatitis C, West Nile, Japanese Encephalitis, Tick borne Encephalitis, St. Louis Encephalitis, Murray Valley Encephalitis, Kyasanur Fever, and any novel as yet undiscovered virus classified as a member of the Flaviviridae. Similarly, the results of Example 16 demonstrate that squalamine systemically administered by either the intraperitoneal or subcutaneous routes, utilizing the phosphate formulation disclosed in this application, to an animal can effectively treat CMV infection and reduce viral titers to undetectable levels. Hence, squalamine can exhibit antiviral activity systemically against both RNA and DNA viruses. The results of Example 16 also demonstrate that squalamine is active against a member of the Herpes Virus family, and supports its use in infections caused by other members of the Herpes family, including Human cytomegalovirus, Herpes Simplex 1, Herpes Simplex 2, Epstein Barr Virus, Varicella Zoster Virus, Roseolovirus (HHV6 and HHV7), Kaposi's Sarcoma Associated Herpes Virus, Cercopithecine herpesvirus-1, Murine gammaherpesvirus-68, the Bovine Herpesviridae, the Canine Herpesviridae, the Equine Herpesviridae, the Feline Herpesviridae, the Duck Herpesviridae, the Chicken Herpesviridae, the Turkey Herpesviridae, Porcine Herpesviridae and any as yet undiscovered virus subsequently classified as a member of the Herpesviridae. Moreover, the results of Example 16 further demonstrate that, by virtue of the measured reduction in viral titers within the spleen, squalamine administered systemically can effectively render virally resistant the cells of the spleen that support CMV infection, which include macrophages. This result supports the use of squalamine in the treatment of all viral diseases in which the macrophage is subject to infection.

Additionally, the results of Example 17 demonstrate the activity of squalamine in treating an infection caused by a member of the Alphavirus family and supports its use in the treatment infection caused by other members of this family, including: Aura virus, Barmah Forest virus, Bebaru virus, Cabassou virus, Chikungunya virus, Eastern equine encephalitis virus, Everglades virus, Fort Morgan virus, Getah virus, Highlands J virus Mayaro virus, Middelburg virus, Mosso das Pedras virus (78V3531, Mucambo virus, Ndumu virus, O'nyong-nyong virus, Pixuna virus, Rio Negro virus, Ross River virus, Salmon pancreas disease virus, Semliki Forest virus, Sindbis virus, Southern elephant seal virus, Tonate virus, Trocara virus, Una virus, Venezuelan equine encephalitis virus, Western equine encephalitis virus, Whataroa virus, as well as any as yet undiscovered virus subsequently classified as a member of the Alpaviridae. Similarly, the results of Example 18 demonstrate that squalamine has direct antiviral activity against Dengue, a non-enveloped RNA virus of the flavivirus family. Because of the similarity in the properties shared by the flavivirus family, in addition to Yellow Fever and Dengue, squalamine would be expected to be active against Hepatitis C, West Nile, Japanese Encephalitis, Tick borne Encephalitis, St. Louis Encephalitis, Murray Valley Encephalitis, Kyasanur Fever, and any novel as yet undiscovered virus classified as a member of the Flaviviridae.

Moreover, the results of Example 19 demonstrate that squalamine can exert antiviral activity against a human Hepatitis B virus infection of human liver. The experiment demonstrates that squalamine can inhibit the early phase of infection as well as the production of virus of cells already infected. These data support the use of squalamine for the treatment of acute and chronic viral hepatitis caused by Hepatitis B. In addition, the results of Example 20 demonstrate that squalamine can exert antiviral activity against a human Hepatitis Delta virus infection of human liver. These data support the use of squalamine for the treatment of acute and chronic viral hepatitis caused by Hepatitis Delta virus. Since Hepatitis B and D frequently co-infect the same individual, these data would support use of squalamine for the treatment of both infections concurrently. The results of Example 20 also demonstrate that squalamine inhibits the replication of both Hepatitis B virus and Hepatitis D virus in primary human hepatocytes, two viruses that differ in their structure, mode of entry, and replicative biology, a result anticipated by the proposed antiviral mechanism of squalamine. These results strongly suggest that squalamine should be effective against other viral infections of the human liver caused by the common Hepatitis viruses: Hepatitis A virus, Hepatitis E, Hepatitis F and Hepatitis G, and any other viral infection of the hepatocyte.

Finally, the results of Example 21 demonstrate that squalamine inhibited HIV infection by about 50% at a concentration of 30 µg/ml compared with vehicle alone, with no evidence of toxicity apparent. At 20 µg/ml inhibition of about 20% was observed. These data support the use of squalamine for the treatment of HIV and other retroviral infections. In addition these data demonstrate that squalamine can block the infectivity of enveloped viruses that enter cells via a pH independent fusion process. Thus, these data support the use of squalamine in the treatment of viral infections caused by viruses such as the retroviridae and the paramyxoviridae, including: Newcastle disease virus, Hendravirus, Nipah virus, measles virus, Rinderpest virus, Canine distemper virus, Sendai virus, Human parainfluenza 1, 2, 3, 4, mumps virus, Menangle virus, Tioman virus, Tuhokovirus 1,2,3, Human respiratory syncytial virus, avian pneumovirus, human metapneumovirus; viruses such as the picornaviridae, including: Human enterovirus A,B,C,D, Human rhinovirus A,B,C, Encephalomyocarditis virus, Theilovirus, Foot and mouth virus, Equine rhinitis A virus, Bovine Rhinitis B virus, Hepatitis A virus, Human Parechovirus, Ljungan virus, Aichi virus, Teschovirus, Sapeloviris, Senecavirus, Tremovirus, Aviheptovirus; viruses such as the rotoviridae, including: rotavirus A,B,C,D,E; viruses such as the papovaviridae.

In another embodiment of the invention, the condition to be treated is a chronic disease suspected to be of viral origin. For example, the condition to be treated can be multiple sclerosis, Type I diabetes, Type II diabetes, atherosclerosis, cardiomyopathies, Kawaski disease, aplastic anemia, etc.

In another embodiment of the invention, combination methods of treating or preventing a viral infection are described. The combination methods comprise: (1) administering a therapeutically effective amount of squalamine, a derivative, a squalamine isomer or prodrug, or a pharmaceutically equivalent salt thereof to a subject in need; and (2) administering a conventional antiviral drug. The squalamine composition and conventional antiviral drug can be administered sequentially or simultaneously. If squalamine or a conventional antiviral drug are administered sequentially, either squalamine or the conventional antiviral drug can be administered first.

1. Aminosterol's Proposed Mechanism for Treating and Preventing Viral Infections To date, a hypothesis that explains the diversity of the aminosterol squalamine's effects has not been reported. While not wishing to be bound by any particular theory, the inventor believes that squalamine exerts its effects by interrupting a key step in the pathways involved in actin dynamics, which it achieves by an unprecedented mechanism. Squalamine does so by integrating in the cellular membrane, profoundly altering the overall charge of that membrane, and causing displacement of key proteins bound to the membrane through electrostatic interactions and required for actin remodeling to occur. Thus, upon entry into a cell, squalamine profoundly alters the behavior of the circuitry involved in control of the actin cytoskeleton. Most viruses must exert control over the actin cytoskeleton to gain entry into the cell they target. This alteration by squalamine effectively "closes the door" to viral entry into the cell. This is because a substance that interrupts the actin remodeling circuitry of a target cell utilized by a virus for infection makes the cell "resistant" so long as the disruptive effects persist.

The basic mechanism of action of squalamine should be operative in any cell into which squalamine can gain entry. Thus, squalamine can prevent viral infection of any cell into which squalamine can gain entry. Moreover, because of the broad tissue distribution of squalamine, the compound can alter the virulence of a virus by interfering with its infectivity of any number of tissues in the animal, a "whole animal" effect that might be missed in a simple cellular screen. Indeed, squalamine represents a class of antiviral that achieves its therapeutic effect by creating a state of viral resistance within the treated animal, rather than by directly targeting a viral enzyme or protein. During this period of squalamine resistance, viral particles, unable to infect tissues, would be cleared and destroyed by the cellular mechanisms that are normally engaged to dispose of particles of their size and composition (i.e., phagocytic destruction by neutrophils, macrophages, and the reticuloendothelial system). Furthermore, as a consequence of the mechanism proposed for the antiviral activity of squalamine, which involves inhibition of cellular circuitry used by viruses to remodel the actin cytoskeleton to permit invasion, squalamine would be expected to exhibit a very broad spectrum of activity, covering viruses of all classes, regardless of their genome composition (RNA vs DNA viruses).

In the case of squalamine, the "resistance" state should last as long as the compound persists in circulation, that being several hours. Based on the known pharmacokinetics of squalamine in rodents, dogs and humans, following administration the compound should rapidly gain entry to a wide range of cells, remain in intracellular sites for between minutes to hours, and eventually traffic out of the cell, unmetabolized, re-entering the circulation, to then be transported into the hepatocyte via its basolateral surface, passage through the cell and subsequently transported from the apical surface of the hepatocyte into the biliary tract.

FIGS. 3A and 3B show the physical changes in cell structure upon exposure to squalamine. More particularly, FIG. 3A shows a picture of a cell before exposure to squalamine. The net negative charge at the cell surface is clearly depicted. After exposure to squalamine, as shown in FIG. 3B, squalamine integrates into the cellular membrane, profoundly altering the overall charge of that membrane, and causing displacement of key proteins bound to the membrane through electrostatic interactions and required for actin remodeling to occur. It is this change in the cell structure which inhibits viral infection of the cell. Specifically, viruses seek the negatively charged cell surface as a "gateway" to the cell for infection. Squalamine effectively closes the gateway by changing the charge and structure of the cell membrane.

Lack of Resistance: Antiviral drug resistance is a significant problem encountered with treating and preventing viral infections. Antiviral resistance means that a virus has changed in such a way that the antiviral drug is less effective in treating or preventing illnesses caused by the virus. Virally encoded drug resistance has been documented against nearly all compounds with antiviral activity. Drug resistance is defined as a reduced susceptibility to a drug in a laboratory culture system and is expressed as an altered $IC_{50}$ or $IC_{90}$ (drug concentration required to inhibit viral growth by 50% or 90% respectively). This is termed the phenotype. This phenotype is determined by specific mutations in the viral genome (the genotype), which leads to alterations in the viral target protein (for example, HIV reverse transcriptase) or the viral drug activator (for example, herpes simplex thymidine kinase). The high rate of replication of some viruses determines that many of these genetic variants will already exist in untreated infected people. This is consequent on an inherent error rate of viral polymerases, especially for RNA viruses such as HIV and influenza, which replicate the viral genome. A wide range of viral variants, including those with mutations associated with drug resistance, will therefore be present. This collection of variants in one person is termed the viral quasispecies, with the "fittest" virus representing the majority population. The use of an antiviral drug will provide a selective pressure for the preferential growth of variants with a reduced susceptibility to drugs in accordance with Darwinian evolutionary principles. The emergent drug resistant virus will be the fittest in the presence of drug. Some drug resistant viruses, however, seem not to replicate as well as wild type virus (in the absence of drug). In some cases, multiple mutations are required for the development of high level resistance, and insufficient suppression of viral replication by antiviral drugs will predispose to their sequential acquisition. Pillay et al., "Antiviral drug resistance," *Public Health Laboratory Service Antiviral Susceptibility Reference Unit, Division of Immunity and Infection*, University of Birmingham Medical School, Birmingham B15 2TT, http://www.bmj.com/content/vol317/issue7159/fulltext/supplemental/660/index.shtml, accessed on Oct. 21, 2009.

In contrast to traditional antiviral therapies, viruses are not expected to develop resistance to squalamine. This is because unlike conventional antiviral therapies, squalamine does not act upon a single mechanism by which a virus infects a cell. Rather, squalamine changes the cell structure for a period of time during which the virus cannot infect the cell. In contrast, certain anti-HIV drugs target the CD4 receptor and other antiviral drugs target inhibition of replication. Viral variants can circumvent each of these targeted antiviral therapies. In one embodiment of the invention, squalamine does not demonstrate an altered $IC_{50}$ or $IC_{90}$ (drug concentration required to inhibit viral growth by 50% or 90% respectively) over time. In other embodiments of the invention, squalamine demonstrates an $IC_{50}$ or $IC_{90}$ which does not increase by more than 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, or 30% over time. In other embodiments of the invention, the time period over which the change in $IC_{50}$ or $IC_{90}$ (or lack thereof) is measured is 1 week, 2 weeks, 3 weeks, 4 weeks, 1 month, 1.5 months, 2 months, 2.5 months, 3 months, 3.5 months, 4 months, 4.5 months, 5 months, 5.5 months, 6 months, 6.5 months, 7 months, 7.5 months, 8 months, 8.5 months, 9 months, 9.5 months, 10 months, 10.5 months, 11 months, 11.5 months, 12 months, 1 year, 1.5 years, 2 years, 2.5 years, 3 years, 3.5 years, 4 years, 4.5 years, or 5 years.

Toxicity: Conventional antiviral agents are generally designed to target viral specific enzymes, such as RNA and DNA polymerases, proteases, or glycosidases; and as a consequence the drug inhibits the activity of the viral enzyme to a far greater extent than it does to analogous human enzymes, required for normal cellular functioning. In many instances toxicity develops as a consequence of the residual activity of the agent towards the analogous enzymes of the host. The experience collected to date involving the administration of squalamine to humans suggests that the compound has an acceptable therapeutic index, a property that further enhances the utility of the invention disclosed herein.

B. Microbial Infections

The present invention is directed to methods of treating and/or preventing microbial infections, and in particular pathogenic microorganisms, comprising administering a therapeutically effective amount of an aminosterol phosphate composition to a subject in need. As noted above, this method encompasses using an aminosterol phosphate composition in combination with conventional antimicrobial treatments to treat and/or prevent infections. A "subject in need" is a human or animal at risk of a microbial infection, or which has contracted a microbial infection.

As used herein the term "microorganism" refers to microscopic organisms and taxonomically related macroscopic organisms within the categories of algae, bacteria, fungi (including lichens), protozoa, viruses, and subviral agents. The term microorganism encompasses both those organisms that are in and of themselves pathogenic to another organism (e.g., animals, including humans, and plants) and those organisms that produce agents that are pathogenic to another organism, while the organism itself is not directly pathogenic or infective to the other organism. As used herein the term "pathogen," and grammatical equivalents, refers to an organism, including microorganisms, that causes disease in another organism (e.g., animals and plants) by directly infecting the other organism, or by producing agents that causes disease in another organism (e.g., bacteria that produce pathogenic toxins and the like).

1. Bacterial Infection

The bacterial infection to be treated and/or prevented can be due to a gram negative bacteria, gram positive bacteria, *Mycobacteria*, bacterial spore, or any combination thereof. Pathogenic bacteria are a major cause of human death and disease and cause infections such as tetanus, typhoid fever, diphtheria, syphilis, cholera, foodborne illness, leprosy and tuberculosis. Examples of gram positive bacteria include, but are not limited to genera such as *Staphylococcus, Streptococcus, Enterococcus*, (which are cocci) and *Bacillus, Corynebacterium, Nocardia, Clostridium, Actinobacteria*, and *Listeria*. Examples of gram negative bacteria include, but are not limited to, *Escherichia coli, Salmonella, Shigella, Enterobacteriaceae, Neisseria, Pseudomonas, Moraxella, Helicobacter, Stenotrophomonas, Bdellovibrio*, acetic acid bacteria, *Legionella* and alpha-proteobacteria as *Wolbachia* and many others. Other notable groups of Gram-negative bacteria include the cyanobacteria, spirochaetes, green sulfur and green non-sulfur bacteria. Medically relevant Gram-negative bacilli include a multitude of species. Some of them primarily cause respiratory problems (*Hemophilus influenzae, Klebsiella pneumoniae, Legionella pneumophila, Pseudomonas aeruginosa*), primarily urinary problems (*Escherichia coli, Proteus mirabilis, Enterobacter cloacae, Serratia marcescens*), and primarily gastrointestinal problems (*Helicobacter pylori, Salmonella enteritidis, Salmonella typhi*). Gram-negative bacteria associated with nosocomial infections include *Acinetobacter baumannii*, which cause bacteremia, secondary meningitis, and ventilator-associated pneumonia in intensive care units of hospital establishments. Relevant *Mycobacteria* include *M. tuberculosis* complex (MTBC), *M. tuberculosis, M. bovis, M. africanum*, and *M. microti; M. leprae, M. avium* complex, *M. avium paratuberculosis, M. avium sylvaticum*, or any of the Mycobacterial species demonstrated to cause disease in man and/or animals.

2. Fungal Infections

The fungal, yeast and/or mold infection to be treated, prevented, and/or cured may be a tinea infection, dermatophytoses, or a dermatophytoma. Examples of fungal microorganisms include, but are not limited to, *Trichophyton* spp., *Epidermophyton* spp., *Fusarium* spp., *Aspergillus* spp., *Paecilomyces* spp., *Acremonium* spp., *Scytalydium* spp., *Scopulariopsis* spp., *Scedosporium* spp., *Alternaria* spp., *Epicoccum* spp., *Curvularia* spp., *Candida* spp., *Phoma* spp., *Chaetomium* spp., and *Microsporum* spp.

Molds include, but are not limited to infections caused by the fungi *Acremonium* spp., *Aspergillus* spp. (e.g., *A. sydowii, A. terreus, A. niger*), *Fusarium* spp. (e.g., *F. oxysporum, F. solani, F. semitectum*), *Scopulariopsis* spp. (e.g., *Scopulariopsis brevicaulis*), *Scedosporuim* spp., *Alternaria* spp., *Paecilomyces lilacinus, Epiccocum nigrum, Phoma* spp. *Chaetomium* spp., *Curvularia* spp., *Onychocola canadensis*, and *Scytalidium* spp., (e.g., *S. dimidiatum*).

Yeast, as defined herein, include, but are not limited to, *Candida* species causing yeast infections.

C. Cancer

The present invention is directed to methods of treating malignant and cancerous tumors, comprising administering a therapeutically effective amount of an aminosterol phosphate composition to a subject in need. A "subject in need" is a human or animal having a malignant and cancerous tumor. As noted above, this method encompasses using an aminosterol phosphate composition in combination with conventional cancer treatments to treat tumors.

Examples of tumors that can be treated with the compositions of the invention include, but are not limited to, breast, brain, lung (e.g., non-small cell lung cancer), and CNS. An example of a solid brain tumor that can be treated with a composition according to the invention is a malignant glioma. Other examples of cancers that can be treated with compositions according to the invention include, but are not limited to, prostate cancer.

EXAMPLES

The following examples are provided to illustrate the present invention. It should be understood, however, that the invention is not to be limited to the specific conditions or details described in these examples. Throughout the specification, any and all references to a publicly available document, including a U.S. patent, are specifically incorporated by reference.

Example 1

Striking Insolubility of Squalamine in the Presence of Inorganic Phosphate and Polyphosphate, but not with Other Common Inorganic Anions The solubility of various squalamine salts was examined to establish a salt form that was partially soluble in water.

A solution of squalamine lactate was prepared in water to a concentration of 10 mg/ml. To 0.1 ml of this solution, 1 volume of a 0.1M solution of various organic and inorganic anions was added. Insolubility of the salt form was scored by the change in the solution from clear/transparent to turbid/cloudy. The results are shown in Table 1, below.

TABLE 1

| Salt | Turbidity |
| --- | --- |
| Sodium phosphate, pH 7.4 | yes |
| Potassium phosphate, pH 7.4 | yes |
| Magnesium phosphate, pH 7.4 | yes |

TABLE 1-continued

| Salt | Turbidity |
| --- | --- |
| Sodium pyrophosphate | yes |
| Sodium triphosphate | yes |
| Sodium acetate | no |
| Sodium chloride | no |
| Sodium lactate | no |
| Sodium gluconate | no |
| Sodium sulfate | no |
| Sodium pyruvate | no |
| Sodium citrate | no |
| Sodium mesylate | no |
| Sodium trifluoracetate | no |
| Sodium carbonate | no |
| Sodium fluoride | no |
| Sodium iodate | no |
| Sodium nitrate | no |
| Glucose 6-phosphate | no |
| Glycerol 2-phosphate | yes |

The insolubility of squalamine in the presence of phosphate, pyrophosphate and polyphosphate is not observed with other common anions.

Example 2

This example evaluated whether an organic phosphate ester could complex with squalamine to generate a weakly soluble salt. Certain organic phosphate esters, such as glycerol-2-phosphate appear to form weakly soluble salts with squalamine, while others such as Glucose-6-phosphate do not. This difference is likely due to the degree of steric hindrance imposed by the organic moiety on electrostatic interactions between the cationic amino groups of the polyamine tail of squalamine and the anionic oxygens of the phosphate.

To determine the approximate molar ratios of squalamine and phosphate that comprise the weakly soluble salt, 50 mg of squalamine ("active") (80 micromoles) lyophilized in vials was dissolved in 3 ml of water. Sodium phosphate (1M, pH 7.7) was added to each vial to 10 mM, 25 mM, 35 mM, and 50 mM, corresponding to 30, 75, 105, and 150 micromoles Phosphate. Samples containing 30 and 75 micromoles of phosphate were milky and turbid, while those containing 105 and 150 formed heavy flocculent precipitates. Thus, the poorly soluble complex formed between 75 and 105 micromoles of phosphate.

From this example it can be concluded that the weakly soluble salt between phosphate and squalamine is a 1:1 complex between the phosphate anion and the squalamine molecule, as shown in the structure below:

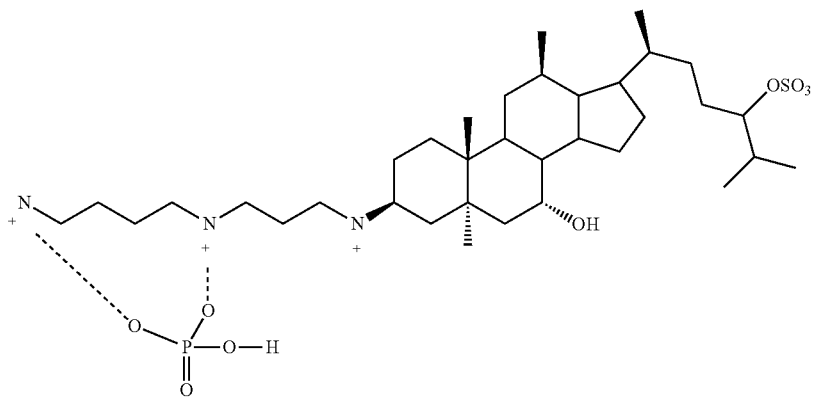

Example 3

To determine the approximate molar ratios of squalamine and pyrophosphate that comprise the weakly soluble pyrophosphate salt, 50 mg of squalamine ("active") (80 micromoles) lyophilized in vials was dissolved in 3 ml of water. Sodium pyrophosphate (1M, pH 7.7) was added to each vial to 1 mM, 2 mM, 4 mM, 6 mM, 10 mM, 25 mM, 35 mM, and 50 mM, corresponding to 3, 6, 12, 24, 30, 75, 105, and 150 micromoles Phosphate. Samples containing 3, 6, 12, 24 and 30 micromoles of pyrophosphate were milky, while those containing 75, 105 and 150 formed heavy flocculent precipitates. Thus, the poorly soluble complex formed between 30 and 75 micromoles of pyrophosphate.

From this example it can be concluded that the weakly soluble salt between pyrophosphate and squalamine a 1:2 complex between the pyrophosphate anion and two squalamine molecules, as shown in the structure below:

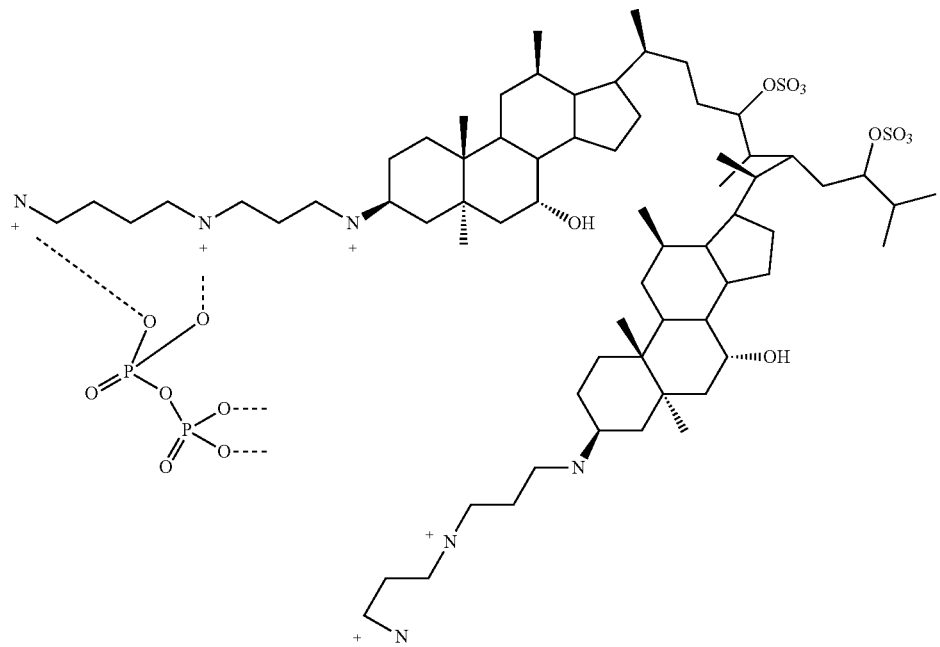

Preparation of Squalamine Phosphate

Squalamine Phosphate can be prepared simply by adding a soluble phosphate salt (i.e., sodium, potassium, ammonium) to a solution of squalamine.

Example 4

100 mg of squalamine lactate (0.16 mmol) was dissolved in 1 ml water. 0.48 mmol of a 1M sodium phosphate solution in water (pH 7.4) was added. A milky suspension formed. 0.5 ml of ethanol was added to begin the washing of the precipitate, and the precipitate was spun down. The precipitate was washed in absolute ethanol and dried.

Example 5

100 mg of squalamine lactate (0.16 mmol) was first dissolved in 1 ml water. 0.16 mmol of a 1M sodium phosphate solution in water (pH 7.4) was then added. A turbid milky suspension formed. The suspension was administered directly as the formulation.

Example 6

To 100 mg of squalamine lactate (0.16 mmol), 1 ml of a solution of 0.16M sodium phosphate (pH 7.4) in 5% dextrose was added. A milky suspension formed. The suspension was either administered directly as the formulation or the squalamine phosphate was recovered and resuspended for use as described in Example 4.

Example 7

To 50 mg of squalamine lactate (0.08 mmol), 5 ml of a solution of 0.016M sodium phosphate (pH 7.4) in 5% dextrose was added. The resulting suspension was administered directly as the formulation. The suspension consisted of irregularly shaped particles that varied in diameter from about 0.5 micron to 1 micron with a density of about 1 gram/ml.

Example 8

To 50 mg of squalamine lactate (0.08 mmol), 5 ml of a solution of 0.08M sodium phosphate (pH 7.4) in 5% dextrose was added. The resulting suspension was administered directly as the formulation. The suspension consisted of birefringent crystalline needles that varied in length from 1 micron to 15 microns, with a diameter of about 1 micron, and with a density greater than 1.05 gram/ml.

Preparation of Squalamine Pyrophosphate

Example 9

100 mg of squalamine lactate (0.16 mmol) was dissolved in 1 ml water. 0.08 mmol of a 1M sodium pyrophosphate solution in water (pH 7.7) was added. A milky precipitate formed.

0.5 volume of ethanol is added to begin the washing of the precipitate, and the precipitate was spun down. The precipitate was washed in absolute ethanol and dried as described in Example 4.

Determination of the Solubility Product of Squalamine Phosphate

Example 10

10 mg of squalamine (16 millimoles) as a phosphate suspension was added to a glass bottle. Water was added gradually, and the suspension vigorously shaken to dissolve the suspension. Squalamine phosphate was fully dissolved after about 250 ml of water had been added.

The final concentration of both squalamine and phosphate in the solution was 16 millimoles/250 ml or 63 micromoles/ml, or 0.063 mM each. The solubility product is defined as the product of the concentration of each ion, calculated in this example to be $3.6 \times 10^{-9}$.

Addition of Inorganic Phosphate to a Squalamine Phosphate Formulation to Reduce Free Concentrations of Squalamine Based on the limited solubility of squalamine phosphate in water, it is possible to reduce the concentration of free squalamine released from the squalamine phosphate suspension by including additional amounts of soluble inorganic phosphate in the suspension.

Using the solubility product of squalamine phosphate, the free concentration of squalamine in the presence of un-dissolved squalamine phosphate and increasing concentrations of additional phosphate can be predicted, as shown in Table 2 below.

TABLE 2

| Phosphate concentration (mM) | Free squalamine concentration (micromolar) | Free squalamine concentration (micrograms/ml) |
| --- | --- | --- |
| No additional (0.063) | 63 | 40 |
| 1.0 | 3.6 | 1 |
| 10 | 0.36 | 0.1 |
| 20 | 0.18 | 0.05 |
| 40 | 0.09 | 0.025 |

Plasma concentrations of inorganic phosphate in man and other mammals are about 1 mM. Since a comparable concentration of free inorganic phosphate would be expected within the extravascular compartment of human tissues, such as muscle or subcutaneous tissue, which are the sites of administration of a suspension of squalamine phosphate, it can predicted by these principles of solubility that the free concentration of squalamine in the immediate vicinity of a dissolving suspension of squalamine phosphate, in the setting of human or mammalian tissue, would be about 1.0 micrograms/ml. This amount is well below the concentration of free squalamine that causes non-specific membrane damage.

Furthermore, administering squalamine phosphate as a suspension in a phosphate containing solution will necessarily reduce the rate of dissolution of the administered squalamine phosphate and reduce the free concentration of squalamine inversely with the concentration of phosphate present in that formulation. Hence, both the rate of dissolution of the suspension and the free concentration of squalamine emanating from the suspended squalamine phosphate can be reduced by increasing the phosphate concentration of the solution used to suspend the squalamine phosphate.

Subcutaneous Administration of Squalamine Phosphate Suspension is Associated with Reduced Local Toxicity Compared with Squalamine Lactate as Demonstrated in Hamsters Example 11

A study was conducted in hamsters to demonstrate the reduction in toxicity associated with the disclosed invention of squalamine phosphate as a preferred salt form for administration of squalamine.

Squalamine was administrated subcutaneously to Syrian hamsters (about 110 grams) at a total daily dose of 60, 30, or 15 mg/kg/d for once daily for seven days. In one cohort, squalamine lactate was administered at a concentration of 10 mg/ml in 5% dextrose. In the other group, the 10 mg/ml squalamine lactate solution in 5% dextrose was adjusted to 50 mM sodium phosphate by the addition of 1M sodium phosphate, creating a turbid suspension, that was used for dosing.

Immediately following subcutaneous administration, animals receiving the squalamine lactate solution exhibited signs of physical discomfort. In contrast, the responses of the animals to administration of squalamine phosphate were identical to those observed following administration of the vehicle buffer (50 mM sodium phosphate in 5% dextrose).

As evident in the results shown in Table 3, below, subcutaneous dosing of squalamine lactate at a concentration of 10 mg/ml caused severe soft tissue lesions at the sites of administration, as recorded 7 days post injection. In surprising contrast, no lesions were seen in the animals injected with a comparable concentration of squalamine phosphate.

TABLE 3

| Group | Dose | Toxicity |
| --- | --- | --- |
| Dextrose solution (D5W) | 0.1 ml | No lesions |
| Squalamine 15 mg/kg/d | 0.15 ml | Mild/moderate by day 1 |
| Squalamine 30 mg/kg/day | 0.3 ml | moderate |
| Squalamine 60 mg/kg/day | 0.6 ml | Severe, open wounds |
| Squalamine 15 mg/kg/day in 50 mM phosphate | 0.15 ml | none |
| Squalamine 30 mg/kg/day in 50 mM phosphate | 0.3 ml | none |
| Squalamine 60 mg/kg/day in 50 mM phosphate | 0.6 ml | none |

Subcutaneous Administration of Squalamine Phosphate in Man is Associated with Markedly Reduced Pain and Local Irritation as Compared to Comparable Dosing of a Solution of Squalamine Lactate Example 12

A 10 mg/ml solution of squalamine lactate was prepared in 5% dextrose. A squalamine phosphate suspension was prepared by adjusting the 10 mg/ml squalamine lactate solution to 50 mM phosphate by addition of 1M sodium phosphate, pH 7.4. 0.1 ml of each preparation was then separately injected into the subcutaneous space between the thumb and second finger of a healthy human subject with a syringe bearing a 26 gauge needle. Within seconds of injection of the squalamine lactate solution, the subject experienced an intense stinging sensation not unlike an insect sting. This sensation persisted for about 20 minutes. Over the course of the following 24 hours the site became tender, swollen, and visibly red. These signs and symptoms persisted for about 1 week, gradually diminishing in intensity.

In contrast, injection of the squalamine phosphate suspension was associated with no pain other than that produced by the needle prick. The site remained free of visible signs of irritation, save for a slight swelling that persisted for about 1 week.

Thus, it is clear that administration of squalamine as a phosphate salt is associated with significantly less local toxicity upon subcutaneous delivery into a human subject as compared to administration of a non-salt form of squalamine, such as squalamine lactate.

Efficacy of Squalamine Phosphate Administered Subcutaneously in the Prevention of Yellow Fever Example 13

The purpose of this example was to determine if squalamine administered in phosphate suspension in vivo retained the efficacy observed with non-phosphate based squalamine formulations. The evaluation was demonstrated in a hamster model of yellow fever.

Materials and Methods

Animals: Female Syrian golden hamsters with an average weight of 110 g were used after a quarantine period of greater than 48 h. Animals were randomly assigned to cages and individually marked with eartags.

Facilities: Experiments were conducted in the biosafety level 3 (BSL-3) animal suite at the Utah State University Laboratory Animal Research Center (LARC). All personnel continue to receive special training on blood-borne pathogen handling by this university's Environmental Health and Safety Office. Standard operating procedures for BSL-3 were used.

Test article: Squalamine was prepared in a 5% dextrose solution (D5W), adjusted to a concentration of 10 mg/ml to yield "squalamine lactate solution," and then adjusted to 50 mM sodium phosphate by addition of 1 M sodium phosphate, pH 7.4, to yield "squalamine phosphate suspension." Ribavirin was provided by ICN Pharmaceuticals, Inc. (Costa Mesa, Calif.), and was prepared in sterile saline. Compounds in solution were prepared just prior to initial administration and stored at 4° C.

Virus: Jimenez, a hamster-adapted YFV strain, was obtained as a generous gift from Robert B. Tesh (University of Texas Medical Branch, Galveston, Tex.). The virus was inoculated into 5 adult female hamsters. The livers of the infected hamsters were removed 3 days post virus injection, and homogenized in a 2× volume of sterile PBS. This liver homogenate had a titer of $10^{6.0}$ 50% cell cultures infectious doses/ml ($CCID_{50}$).

Experimental design: Hamsters were randomly assigned to groups, with 10 included in each and 20 placebo-treated controls. A $10^{-4}$ dilution ($10^{2.0}$ $CCID_{50}$/ml) of the virus was prepared in minimal essential media. Hamsters were injected intraperitoneally (i.p.) with 0.1 ml of the diluted virus (10 $CCID_{50}$/animal). Squalamine was administered subcutaneously at a total daily dose of 15 mg/kg/day given qd beginning −24 h and ending on 6 days post inoculation. Ribavirin was administered i.p. at a dose of 50 mg/kg/d administered bid X 7 days beginning −4 h. Mortality was observed daily for 21 days, and weight was recorded on 0, 3, and 6 dpi. Evaluation of squalamine lactate and squalamine phosphate were conducted as 2 independent complete studies, utilizing placebos and positive controls.

Figure 2:
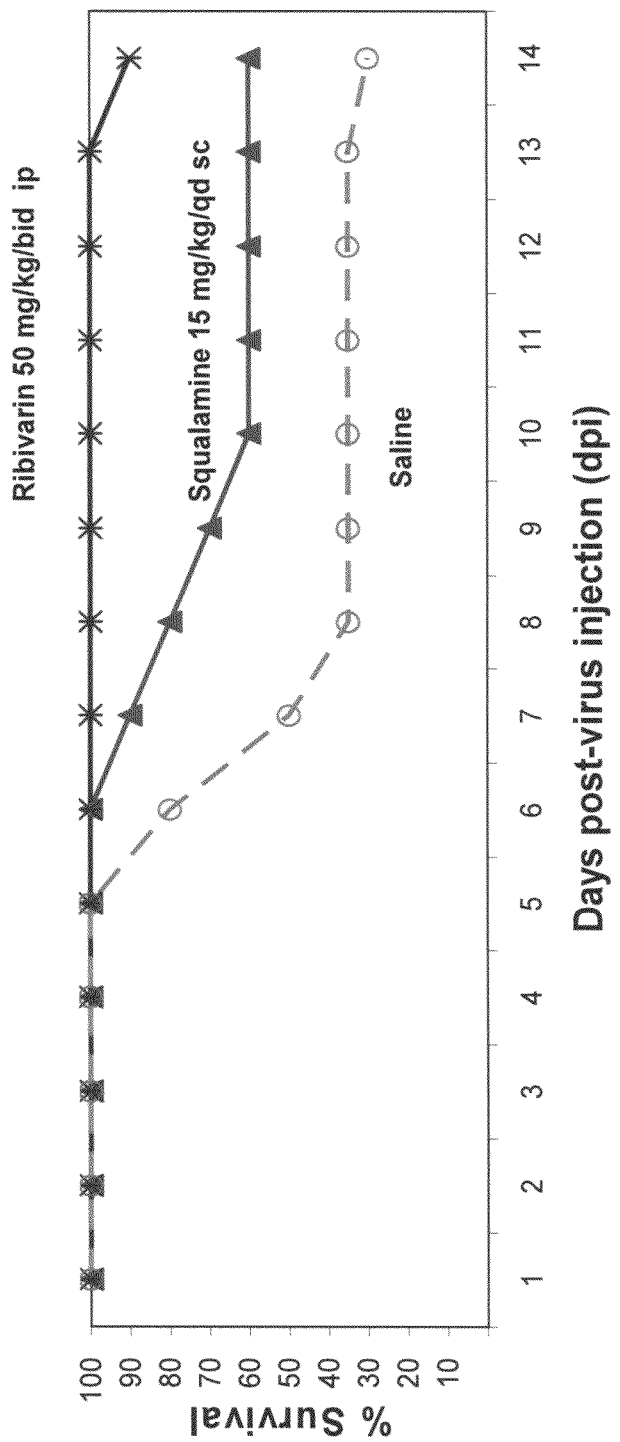
FIG. 2: Shows the percent survival as compared to days post infection (dpi) for three groups of hamsters: (1) Group I, administered squalamine lactate solution in 5% dextrose; (2) Group 2, administered ribavirin, which is the conventional treatment for yellow fever, and (3) Group 3, administered saline as a placebo. Animals were injected with Jimenez, a hamster-adapted yellow fever virus strain. Administration of squalamine lactate was associated with a 60% survival as compared to 30% for the placebo Group.

As shown in FIG. 1, animals receiving squalamine phosphate achieved about 70% survival by day 12 vs 35% for placebo. As shown in FIG. 2, administration of squalamine lactate was associated with a 60% survival, as compared to 30% for placebo.

All animals receiving the subcutaneous dosing of squalamine lactate exhibited severe soft tissue lesions caused by local tissue damage inflicted by squalamine lactate. Those animals receiving squalamine phosphate exhibited injection sites that were normal in appearance.

This example demonstrates the significant in vivo effectiveness of the squalamine phosphate compositions of the invention, and the dramatic elimination or significant reduction in injection site irritation associated with the compositions of the invention.

Example 14

The purpose of this example was to evaluate the effectiveness of the squalamine phosphate formulation, administered subcutaneously, in treating a viral infection, such as Yellow Fever, in a head-to-head comparison with ribavirin, over a comparable dosing schedule. Ribavirin is a nucleoside analogue that is effective in the hamster model when administered via an optimized dosing schedule. Ribavirin is used as an antiviral therapeutic in humans, mainly for the treatment of Hepatitis C, in conjunction with Interferon-α.

Experimental design: Hamsters were randomly assigned to groups, with 10 included in each and 20 placebo-treated controls. A $10^{-4}$ dilution ($10^{2.0}$ $CCID_{50}$/ml) of the virus was prepared in minimal essential media. Hamsters were injected intraperitoneally (i.p.) with 0.1 ml of the diluted virus (10 $CCID_{50}$/animal). Squalamine phosphate suspension was prepared by first dissolving 50 mg squalamine lactate into 3 ml of 5% dextrose, followed by the addition of 2 ml 40 mM sodium phosphate, pH 7.2. The suspension was left to "organize" for several minutes and then was administered subcutaneously (s.c.) at a total daily dose 15 mg/kg/d, given once a day (qd) beginning 24 h before introduction of virus and ending on 6 days post infection (dpi). Ribavirin was administered intraperitonealy (i.p.) at doses of 3. 2, 10, or 32 mg/kg/d administered once daily beginning 24 h before introduction of virus and ending on 6 days post infection (dpi). Mortality was observed daily for 21 days, and weight was recorded on 0, 3, and 6 dpi.

Statistical analysis: Survival data were analyzed using the Wilcoxon log-rank survival analysis and all other statistical analyses were done using one-way ANOVA using a Bonferroni group comparison (Prism 5, GraphPad Software, Inc).

Figure 4:
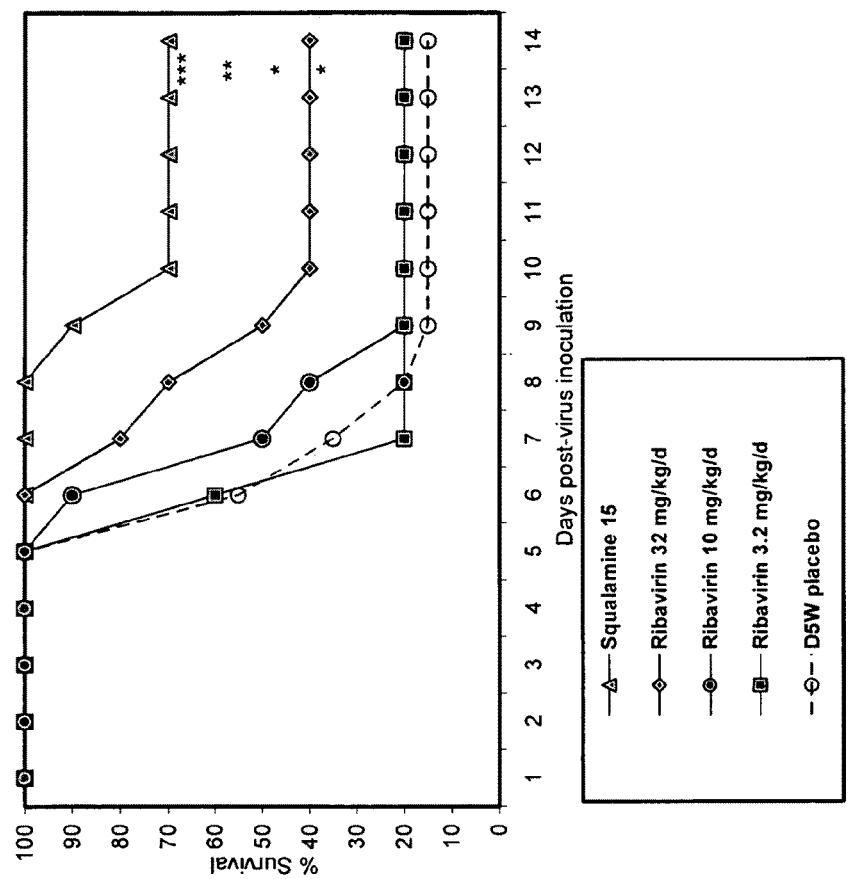
FIG. 4: Shows the results of an in vivo test to determine the effectiveness of squalamine formulated as the phosphate suspension against Yellow Fever in Syrian hamsters in a head-to-head comparison with the antiviral drug ribavirin. Squalamine at 15 mg/kg was administered subcutaneously daily, while ribavirin was administered once daily i.p. at either 3.2, 10, and 32 mg/kg. Squalamine was the most effective treatment, with 70% of the animals surviving, compared with about 10% of those receiving vehicle. Ribavirin was less effective, the maximal dose achieving a survival of 40%.

Results: Treatment with the squalamine phosphate formulation resulted in 70% survival compared with 15% of animals receiving vehicle alone (FIG. 4). About 40% of the animals receiving ribavirin at the highest dose (32 mg/kg/day) survived, while those receiving lower doses fared no better than the placebo-treated cohort.

These results illustrate the effectiveness of the squalamine phosphate formulation, the effectiveness of squalamine as an antiviral agent, and demonstrate that its antiviral activity in an animal is comparable to a well-studied antiviral agent currently in use as a human therapeutic drug against another flavivirus, Hepatitis C.

Example 15

The purpose of this experiment was to evaluate the efficacy of squalamine systemically administered as a phosphate formulation as an antiviral treatment in a setting where the viral infection, such as Yellow Fever, has already been established.

Experimental design: Hamsters were randomly assigned to three groups, with 10 included in each and 20 placebo-treated controls. A $10^{-4}$ dilution ($10^{2.0}$ $CCID_{50}$/ml) of the virus was prepared in minimal essential media. Hamsters were injected into the peritoneum (i.p.) with 0.1 ml of the diluted virus (10 $CCID_{50}$/animal). The squalamine phosphate formulation was prepared as described in example 14. Squalamine phosphate was administered subcutaneously (s.c.) at a total daily dose 15 mg/kg/d, given once a day (qd) beginning 24 h after introduction of virus and ending on 8 days post infection (dpi), 30 mg/kg/d, given once a day (qd) beginning 24 h after introduction of virus and ending on 8 days post infection (dpi), and 30 mg/kg/d, given once a day (qd) beginning 48 h after introduction of virus and ending on 9 days post infection (dpi). Mortality was observed daily for 21 days, and weight was recorded on 0, 3, and 6 dpi.

Statistical analysis: Survival data were analyzed using the Wilcoxon log-rank survival analysis and all other statistical analyses were done using one-way ANOVA using a Bonferroni group comparison (Prism 5, GraphPad Software, Inc).

Figure 5:
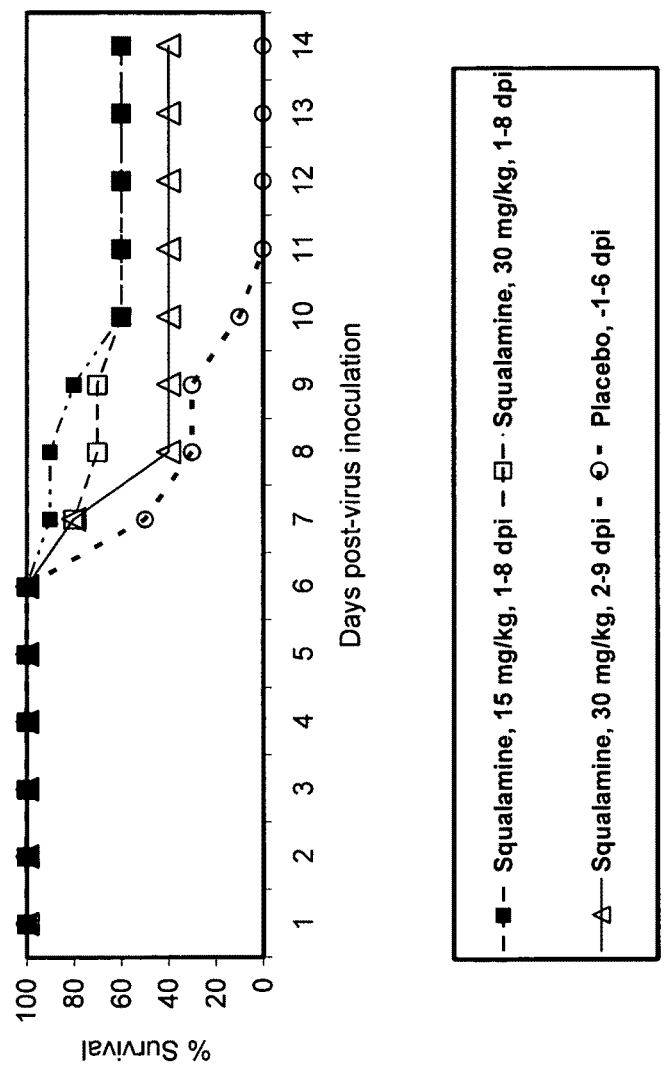
FIG. 5: Shows the results of an in vivo test to determine the effectiveness of squalamine formulated as the phosphate suspension against an established Yellow Fever in Syrian hamsters. Squalamine treatment is shown to cure a lethal infection when administered 1 or 2 days after viral administration.

Results: (FIG. 5) Whereas 100% of animals untreated died of Yellow Fever by day 11 post-infection, 60% of animals treated at 1 dpi with 15 mg/kg/day (s.c.) squalamine for 8 days survived and appeared to be cured as measured by continued survival through day 21. Similarly, 60% of animals treated at 1 dpi with 30 mg/kg/day appeared to have been cured as indicated by survival through day 21. Treatment remained effective even when dosing began on 2 dpi, with 40% of animals cured, when treated with squalamine at 30 mg/kg/day (s.c.) for 9 days.

The results of this example demonstrate that squalamine can be utilized as an effective systemic antiviral therapy in already established viral infection when administered in the squalamine phosphate formulation disclosed in this application. Because of the similarity in the properties shared by the flavivirus family, in addition to Yellow Fever, squalamine could be used to treat infections caused other members of the Flaviviridae including: Dengue, Hepatitis C, West Nile, Japanese Encephalitis, Tick borne Encephalitis, St. Louis Encephalitis, Murray Valley Encephalitis, Kyasanur Fever, and any novel as yet undiscovered virus classified as a member of the Flaviviridae.

Yellow fever virus utilizes a pH dependent entry pathway to initiate infection. Based on the mechanism of action of squalamine and the efficacy of squalamine in the treatment of an established infection caused by Yellow fever, squalamine could be considered for the treatment of other infections caused by viruses that utilize a pH dependent entry pathway such as members of the Orthomyxoviridae including: Influenza A, B, C, Isavirus, Thogotovirus; members of the Rhabdomyoviridae, including: Vesiculovirus, Lyssavirus, Cytorhabdovirus, Nucleorhabdovirus, Novirhabdovirus; members of the Adenoviridae including: all Human Adenovirus types (1-55) and species (A-G,), Atadenovirus, Avidenovirus, Icthadenovirus, Mastadenovirus, Siadenovirus; members of the Parvoviridae; members of the Filoviridae; members of the Iridoviridae; and the Rubella virus.

Example 16

The purpose of this experiment was to evaluate the efficacy in an animal of systemically administered squalamine in the phosphate formulation disclosed in this application against a DNA virus. In this example mice have been infected with murine cytomegalovirus (MCMV), a virus similar to CMV that infects humans.

Experimental design: In this experiment mice were treated 24 hours prior to infection and treatment continued daily for 6 days post infection. Animals were sacrificed on days 3, 7, and 14, organs were harvested, and virus content determined by a standard viral plaque assay. 54 male Balb/c mice were inoculated into the peritoneum (i.p.) with 0.1 ml of a virulent strain of MCMV following a published protocol (Cavanaugh, Deng et al. 2003). 18 animals received 5% dextrose i.p., and served as controls; 18 received 10 mg/kg/day of squalamine i.p., as a 1 mg/ml solution in 5% dextrose; 18 received 10 mg/kg/day of squalamine phosphate prepared as described in Example 14. subcutaneously. On days 3, 7, and 14, 6 animals from each dosing cohort were randomly selected, euthanized and viral titers determined from the liver, spleen, lung, and submaxillary gland.

Statistical analysis: Statistical analyses were done using one-way ANOVA using a Bonferroni group comparison or via Student's T test (Prism 5, GraphPad Software, Inc).

Figure 6:
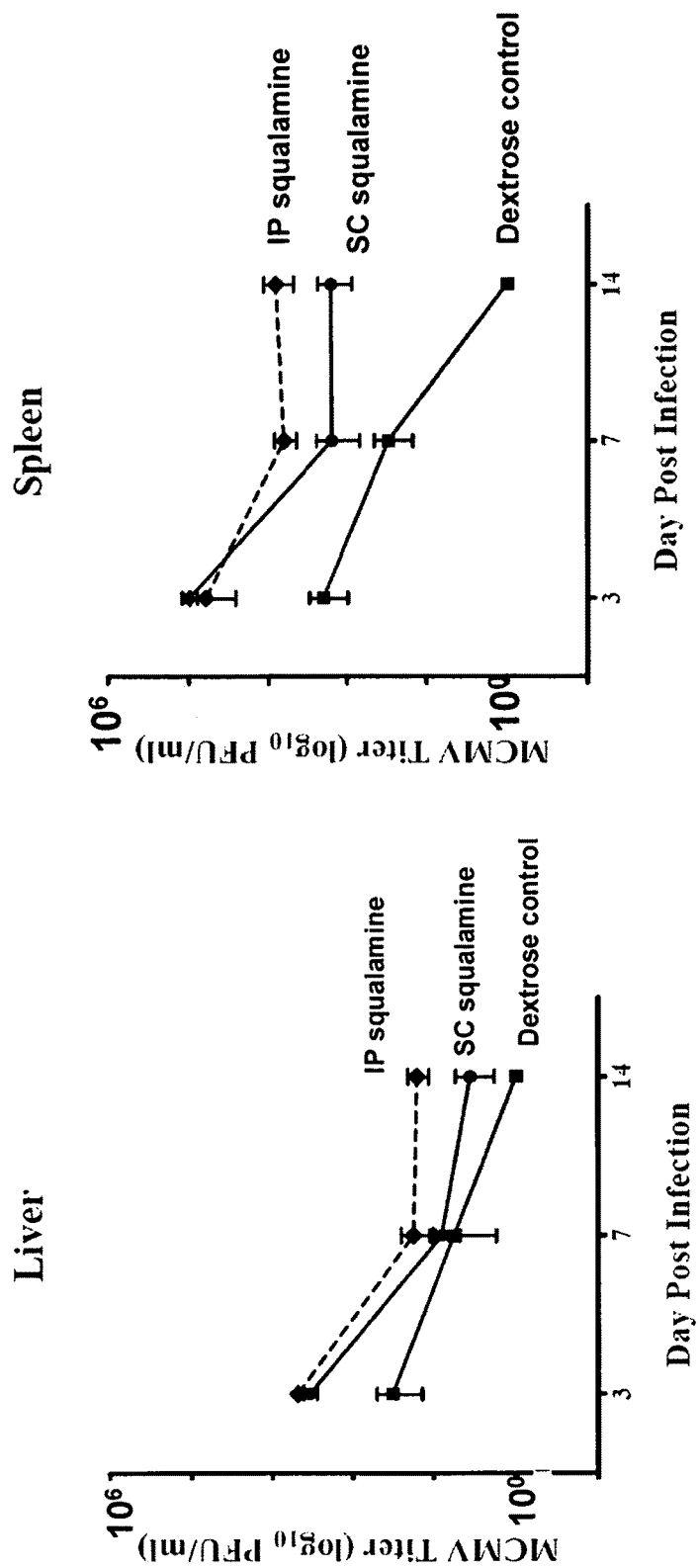
FIG. 6: Shows the results of an in vivo test to determine the effectiveness of squalamine against Cytomegalovirus infection in the mouse. Squalamine, administered at 10 mg/kg/day i.p. and 10 mg/kg/day subcutaneously, as the phosphate suspension is shown to achieve a reduction of viral titers in spleen and liver to undetectable levels in infected animals.

Results: (FIG. 6) At day 3 a greater than 10-fold reduction in viral growth was observed in liver, spleen, and lung in animals that had received squalamine via the i.p. route, with little effect observed in the salivary gland. Between day 3 and 7, viral titers in spleen and liver fell about 10-fold in all groups, with the viral titers in the s.c. and i.p. groups significantly lower than in the control cohort; in contrast, viral titers increased between days 3 and 7 in the lungs and salivary glands, with no significant differences observed between groups. By day 14, 8 days after squalamine had stopped, virus was undetectable in the liver and spleen of animals that had received squalamine i.p., and was significantly reduced in the s.c. treatment group compared with controls. A trend toward reduction in viral titers in lung compared with control was observed in the i.p. treatment group.

The results of this example demonstrate that squalamine systemically administered by either the intraperitoneal or subcutaneous routes, utilizing the phosphate formulation disclosed in this application, to an animal can effectively treat CMV infection and reduce viral titers to undetectable levels. Hence, squalamine can exhibit antiviral activity systemically against both RNA and DNA viruses.

This experiment also demonstrates that squalamine is active against a member of the Herpes Virus family, and supports its use in infections caused by other members of the Herpes family, including Human cytomegalovirus, Herpes Simplex 1, Herpes Simplex 2, Epstein Barr Virus, Varicella Zoster Virus, Roseolovirus (HHV6 and HHV7), Kaposi's Sarcoma Associated Herpes Virus, Cercopithecine herpesvirus-1, Murine gammaherpesvirus-68, the Bovine Herpesviridae, the Canine Herpesviridae, the Equine Herpesviridae, the Feline Herpesviridae, the Duck Herpesviridae, the Chicken Herpesviridae, the Turkey Herpesviridae, Porcine Herpesviridae and any as yet undiscovered virus subsequently classified as a member of the Herpesviridae.

This experiment also demonstrates, by virtue of the measured reduction in viral titers within the spleen, that squalamine administered systemically can effectively render virally resistant the cells of the spleen that support CMV infection, which include macrophages. This result supports the use of squalamine in the treatment of all viral diseases in which the macrophage is subject to infection.

Example 17

The purpose of this experiment was to evaluate the efficacy of systemically administered squalamine as the phosphate formulation against the Eastern Equine Encephalitis Virus, an RNA virus of the alphavirus family.

Experimental design: In this experiment hamsters (Syrian golden) were treated with either 5% dextrose (n=10, each species) or 10 mg/kg/day s.c. squalamine phosphate formulation (n=10), beginning 24 hours prior to infection with EEEV, administered s.c., following a published protocol (Paessler, Aguilar et al. 2004). Squalamine phosphate was prepared as described in Example 14. Treatments continued for 6 days after infection. Plasma viral titers were measured, along with body weights and survival.

Statistical analysis: Survival data were analyzed using the Wilcoxon log-rank survival analysis and all other statistical analyses were done using one-way ANOVA using a Bonferroni group comparison, or via Student's T test (Prism 5, GraphPad Software, Inc).

Figure 7:
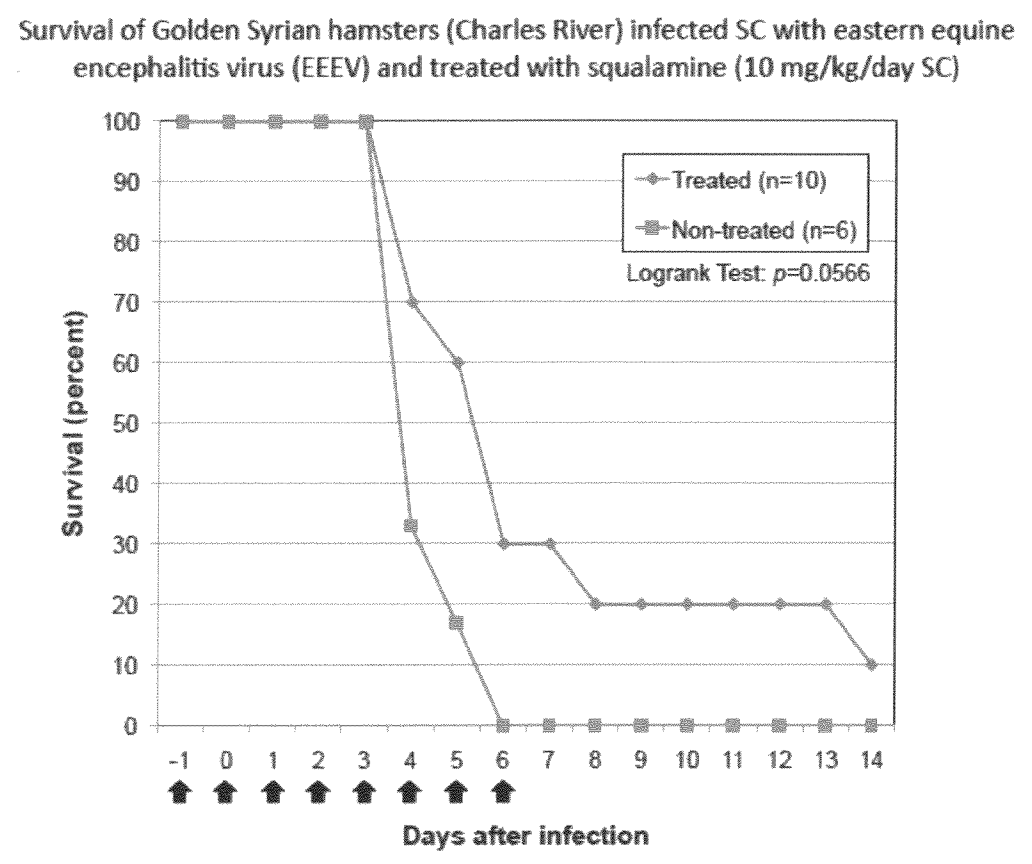
Figure 8:
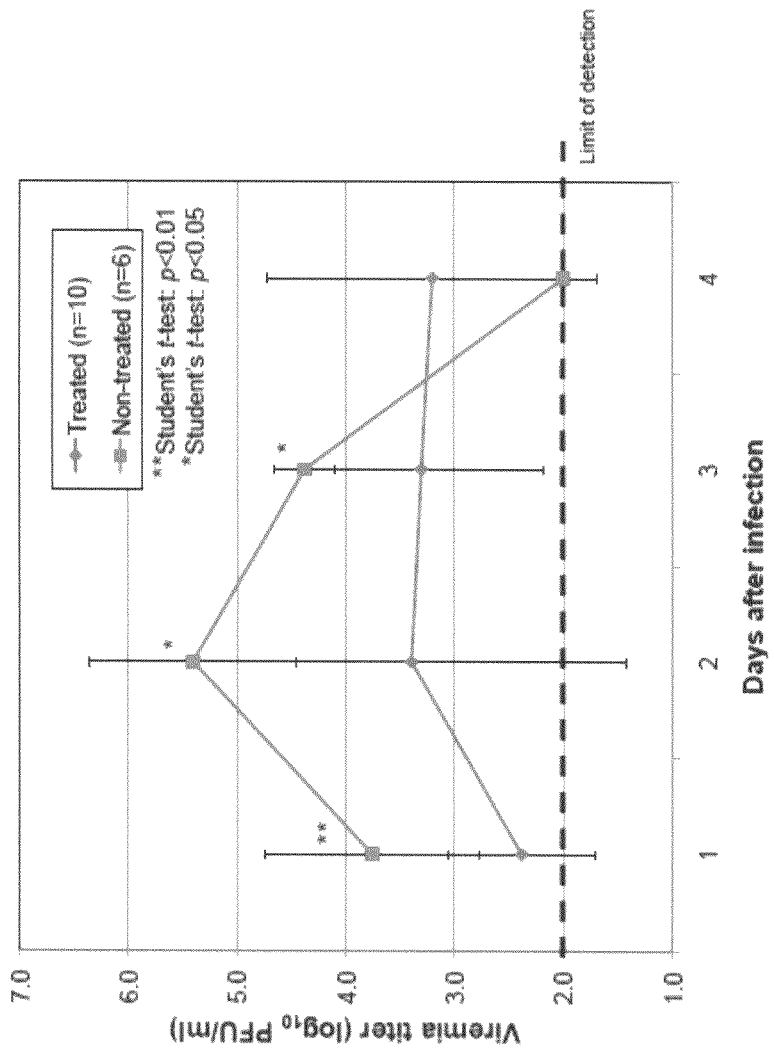
FIG. 8: Shows the results of an in vivo test to determine the effectiveness of squalamine against Eastern Equine Encephalitis virus in Syrian hamsters. Squalamine administered at 10 mg/kg/day s.c. as the phosphate formulation is shown to significantly reduce viremia compared with a vehicle control, in the experiment described in FIG. 8.

Results: Squalamine administration as the phosphate formulation extended survival in the hamster cohort (FIG. 7). At the end of treatment, 6/10 hamsters receiving squalamine were still alive, compared with 0/10 receiving vehicle. Concentration in the bloodstream of the hamster were determined (the mice were not studied since squalamine was ineffective). Plasma concentrations of virus were lower by about 100 fold in hamsters that had received squalamine compared with vehicle over the first 3 days post infection, confirming that squalamine has antiviral activity in an animal, likely the cause of improved survival (FIG. 8). We assume that a more pronounced effect on viremia would be observed with administration of higher squalamine doses.

The results of this example demonstrate that squalamine can effectively reduce the concentration of virus in an animal when administered systemically as the phosphate formulation disclosed in this application This experiment also demonstrates the activity of squalamine in treating an infection caused by a member of the Alphavirus family and supports its use in the treatment infection caused by other members of this family, including: Aura virus, Barmah Forest virus, Bebaru virus, Cabassou virus, Chikungunya virus, Eastern equine encephalitis virus, Everglades virus, Fort Morgan virus, Getah virus, Highlands J virus Mayaro virus, Middelburg virus, Mosso das Pedras virus (78V3531, Mucambo virus, Ndumu virus, O'nyong-nyong virus, Pixuna virus, Rio Negro virus, Ross River virus, Salmon pancreas disease virus, Semliki Forest virus, Sindbis virus, Southern elephant seal virus, Tonate virus, Trocara virus, Una virus, Venezuelan equine encephalitis virus, Western equine encephalitis virus, Whataroa virus, as well as any as yet undiscovered virus subsequently classified as a member of the Alpaviridae.

Example 18

The purpose of this experiment was to demonstrate the antiviral effects of squalamine against Dengue. Dengue is a flavivirus, related to Yellow Fever Virus, and human Hepatitis C virus. The study was conducted in cell culture and utilized as substrate for infection a well studied line of human endothelial cells (HMEC-1) anticipated to be responsive to squalamine based on squalamine's known activity against endothelial cells.

Experimental design: Cells were grown on uncoated glass cover-slips following a published protocol (Zamudio-Meza, Castillo-Alvarez et al. 2009). The cells were pretreated with squalamine for 2 hr at 37° C. prior to viral exposure; virus (multiplicity of infection of 3) remained in contact with cells for 30 minutes at 4° C., followed by 90 minutes at 37° C. The medium was then replaced with fresh medium lacking virus and squalamine and maintained at 37° C. for 48 hrs. Cells were fixed and processed for immunohistochemical detection of viral E protein. Viral E protein expression was used to monitor the early stages of infection.

Figure 9:
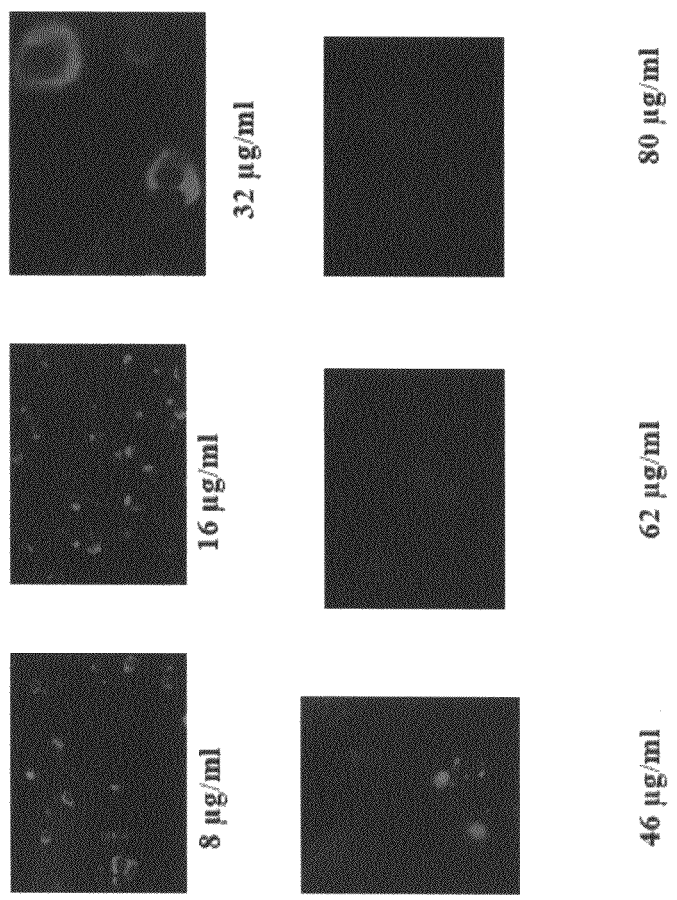
FIG. 9: Shows the results of an in vitro study to assay the antiviral activity of squalamine against Dengue virus. Human microvascular endothelial cells were exposed to Dengue virus in the presence of increasing concentrations of squalamine. Viral infection was monitored by immunofluorescent analysis of the Dengue E protein. At 46 µg/ml, squalamine achieved an inhibition of viral infection of about 80%, with 100% inhibition observed at 62 µg/ml.

Results: Viral infection was markedly diminished at concentrations of about 40 µg/ml (80%), with almost 100% inhibition at 60 µg/ml and higher (FIG. 9). Cell viability was not diminished at the effective squalamine concentrations, based on morphology and appearance under phase contrast.

This experiment demonstrates that squalamine has direct antiviral activity against Dengue, a non-enveloped RNA virus of the flavivirus family. Because of the similarity in the properties shared by the flavivirus family, in addition to Yellow Fever and Dengue, squalamine would be expected to be active against Hepatitis C, West Nile, Japanese Encephalitis, Tick borne Encephalitis, St. Louis Encephalitis, Murray Valley Encephalitis, Kyasanur Fever, and any novel as yet undiscovered virus classified as a member of the Flaviviridae.

Example 19

The purpose of this experiment was to determine the antiviral activity of squalamine against human Hepatitis B virus. The experiment was conducted in vitro, using primary human hepatocytes.

Experimental design: Primary human hepatocytes were established in a 96 well microtiter plate. Squalamine was then added at concentrations of 2, 6 or 20 µg/ml followed by an inoculum of Hep B virus, and then in culture for 16 hours, after which fresh medium was introduced, and the cells maintained in culture for 14 days. In a second experiment, squalamine at 6 or 20 µg/ml was added to the cells at 24 hours post inoculation for a 16 hour exposure, followed by removal of medium, replacement with fresh medium, and continued culture for 14 days. Viral growth was measured by PCR using viral specific primers and normalized to the total RNA extracted from each corresponding well.

Results: Squalamine effectively inhibited HepB viral replication in human primary hepatocytes when added either during the initial exposure of virus to the cells, or at 24 hours. At a concentration of 20 µg/ml squalamine inhibited viral production by 83% when added during initial stages of infection, and by 64% when added at 24 hours; at a concentration of 6 µg/ml squalamine inhibited viral production by 54% when added at the onset of infection, and by 30% when added at 24 hours; squalamine at 2 µg/ml, added only at the outset of infection, inhibited production by 14%.

The experiment demonstrates that squalamine can exert antiviral activity against a human Hepatitis B virus infection of human liver. The experiment demonstrates that squalamine can inhibit the early phase of infection as well as the production of virus of cells already infected. These data support the use of squalamine for the treatment of acute and chronic viral hepatitis caused by Hepatitis B.

Example 20

The purpose of this experiment was to determine the antiviral activity of squalamine against human Hepatitis Delta virus. HDV is a small circular RNA virus that causes hepatitis by itself or in conjunction with Hepatitis B virus. The experiment was conducted in vitro, using primary human hepatocytes.

Experimental design: Primary human hepatocytes were established in a 96 well microtiter plate. Squalamine was then added at concentrations of 20 or 60 µg/ml followed by an inoculum of Hep D virus, and then in culture for 3 hours, after which fresh medium was introduced, and the cells maintained in culture for 7 days. Viral growth was measured by PCR using viral specific primers and normalized to the total RNA extracted from each corresponding well.

Results: Squalamine effectively inhibited Hepatitis Delta viral replication in human primary hepatocytes when added during the initial exposure of virus to the cells. At a concentration of 20 µg/ml squalamine inhibited viral production by 90% when added during initial stages of infection. The 60 µg/ml concentration proved to be cytotoxic in vitro.

The experiment demonstrates that squalamine can exert antiviral activity against a human Hepatitis Delta virus infection of human liver. These data support the use of squalamine for the treatment of acute and chronic viral hepatitis caused by Hepatitis Delta virus. Since Hepatitis B and D frequently co-infect the same individual, these data would support use of squalamine for the treatment of both infections concurrently.

Squalamine inhibits the replication of both Hepatitis B virus and Hepatitis D virus in primary human hepatocytes, two viruses that differ in their structure, mode of entry, and replicative biology, a result anticipated by the proposed antiviral mechanism of squalamine. These results strongly suggest that squalamine should be effective against other viral infections of the human liver caused by the common Hepatitis viruses: Hepatitis A virus, Hepatitis E, Hepatitis F and Hepatitis G, and any other viral infection of the hepatocyte.

Example 21

The purpose of this experiment was to determine the antiviral activity of squalamine against human immunodeficiency virus (HIV).

Experimental design: A line of HeLa cells is utilized that expresses the receptors and co-receptors required for the binding and entry of HIV, namely CXCR4, CD4 and CCR5. The HeLa line also has a luciferase reporter gene driven by the HIV-LTR so if infection occurs luciferase is expressed (Harmon, Campbell et al.). The amount of luciferase made is measured and serves as a measure of infection. The cells are plated and infected in the presence or absence of the squalamine. A strain of vesicular stomatitis virus (VSV) that contains HIV genes required to activate the luciferase gene is utilized as a toxicity control, and should infect the cells equally well with or without the squalamine (unless squalamine also inhibits the infectivity of VSV). Once the cells are infected they incubate for at least 1 day (in the presence of the drug). The virus and drug are removed from the cells and then the cells are lysed with PBS+0.2% TritonX-100. Luciferase assays are done on the lysates to measure the level of infection.

Results: Squalamine inhibited HIV infection by about 50% at a concentration of 30 µg/ml compared with vehicle alone, with no evidence of toxicity apparent. At 20 µg/ml inhibition of about 20% was observed.

These data support the use of squalamine for the treatment of HIV and other retroviral infections. In addition these data demonstrate that squalamine can block the infectivity of enveloped viruses that enter cells via a pH independent fusion process. Thus, these data support the use of squalamine in the treatment of viral infections caused by viruses such as the retroviridae and the paramyxoviridae, including: Newcastle disease virus, Hendravirus, Nipah virus, measles virus, Rinderpest virus, Canine distemper virus, Sendai virus, Human parainfluenza 1, 2, 3, 4, mumps virus, Menangle virus, Tioman virus, Tuhokovirus 1,2,3, Human respiratory syncytial virus, avian pneumovirus, human metapneumovirus; viruses such as the picornaviridae, including: Human enterovirus A,B,C,D, Human rhinovirus A,B,C, Encephalomyocarditis virus, Theilovirus, Foot and mouth virus, Equine rhinitis A virus, Bovine Rhinitis B virus, Hepatitis A virus, Human Parechovirus, Ljungan virus, Aichi virus, Teschovirus, Sapeloviris, Senecavirus, Tremovirus, Avihepatovirus; viruses such as the rotoviridae, including: rotavirus A, B, C, D, E; viruses such as the papovaviridae.

Preparation of Salt of glycerol-2-phosphate and Squalamine

Example 22

100 mg of squalamine lactate (0.16 mmol) was dissolved in 1 ml water. 0.32 mmol of a 1M solution of glycrol-2-phosphate in water was added. A heavy precipitate formed. 0.5 volume of ethanol was added to begin the washing of the precipitate, and the precipitate was spun down. On microscopic examination the suspension consisted of needle-like crystals of about 0.5 microns in diameter, and varying in length from 1-100 microns. The precipitate was washed in absolute ethanol and dried as described in Example 4.

Preparation of the Phosphate Salt of Other Aminosterols: Aminosterol 1436

Example 23

100 mg of Aminosterol 1436 lactate (0.16 mmol) was dissolved in 1 ml water. 0.48 mmol of a 1M sodium phosphate solution in water (pH 7.4) is added. A heavy precipitate formed. 0.5 volume of ethanol was added to begin the washing of the precipitate, and the precipitate was spun down. The precipitate was washed in absolute ethanol and dried.

Since the salt is an electrostatic complex between the polyamine moiety and phosphate, any aminosterol containing a net positive charge due to the presence of free polyamine nitrogen can be transformed into a weakly soluble salt as disclosed in this invention. Thus, the invention is broadly applicable to squalamine and squalamine derivatives, as disclosed herein.

Favorable and Unanticipated Solubility of the Disclosed Aminosterol Phosphate Suspension in the Presence of Serum Albumin Example 24

A property of the squalamine phosphate formulation that is not evident is its rapid dissolution in the presence of serum albumin. This property can be demonstrated as follows.

Two solutions are prepared, one consisting of 0.9% NaCl, the other 0.9% NaCl with 30 mg/ml bovine serum albumin (the approximate concentration of albumin in human blood). 10 ml of each solution are added to separate test tubes. Into each solution a squalamine phosphate suspension (10 mg/ml, prepared as in Example 14) is added dropwise. Addition of the squalamine phosphate suspension to the test tube containing 0.9% NaCl yields a cloudy suspension, proportionally diluted by the larger volume. In contrast, addition of the squalamine phosphate suspension to the test tube containing 0.9% and serum albumin rapidly clarified to yield a clear solution, and remained clear even as the concentration of squalamine phosphate reached 1 mg/ml. Clarification takes place within several seconds following mixing.

This phenomenon can readily be explained as a consequence of the affinity of squalamine (and the other aminosterols) for serum albumin, and the resulting displacement of the equilibrium (consisting of the system of albumin, squalamine and phosphate) in favor of albumin bound squalamine. Thus, as a particle of squalamine phosphate dissociates into free squalamine and phosphate, the free squalamine molecule is bound by an albumin molecule, preventing its re-capture by a phosphate molecule. The concentration of free squalamine in this system will never exceed that established by the solubility properties expected for squalamine phosphate.

The magnitude of the affinity of squalamine for serum albumin insures that the squalamine phosphate suspension will fully dissolve after parenteral administration, rather than remain particulate, even when dosed intravenously.

The solubility properties of the aminosterol phosphate salts disclosed herein are uniquely poised in magnitude to provide utility as therapeutic formulations, sufficiently soluble to dissolve to achieve a therapeutic effect, but sufficiently insoluble to limit the free concentration of the aminosterol within a non-cytotoxic range.

It will be apparent to those skilled in the art that various modifications and variations can be made in the methods and compositions of the present invention without departing from the spirit or scope of the invention. Thus, it is intended that the present invention cover the modifications and variations of this invention, provided they come within the scope of the appended claims and their equivalents.

REFERENCES

Ahima, R. S., H. R. Patel, et al. (2002). "Appetite suppression and weight reduction by a centrally active aminosterol." Diabetes 51(7): 2099-104.

Bhargava, P., J. L. Marshall, et al. (2001). "A phase I and pharmacokinetic study of squalamine, a novel antiangiogenic agent, in patients with advanced cancers.". Clin Cancer Res 7(12): 3912-9.

Connolly, B., A. Desai, et al. (2006). "Squalamine lactate for exudative age-related macular degeneration." Ophthalmol Clin North Am 19(3): 381-91, vi.

Hao, D., L. A. Hammond, et al. (2003). "A Phase I and pharmacokinetic study of squalamine, an aminosterol angiogenesis inhibitor." Clin Cancer Res 9(7): 2465-71.

Herbst, R. S., L. A. Hammond, et al. (2003). "A phase I/IIA trial of continuous five-day infusion of squalamine lactate (MSI-1256F) plus carboplatin and paclitaxel in patients with advanced non-small cell lung cancer." Clin Cancer Res 9(11): 4108-15.

Moore, K. S., S. Wehrli, et al. (1993). "Squalamine: an aminosterol antibiotic from the shark." Proc Natl Acad Sci USA 90(4): 1354-8.

Sills, A. K., Jr., J. I. Williams, et al. (1998). "Squalamine inhibits angiogenesis and solid tumor growth in vivo and perturbs embryonic vasculature." Cancer Res 58(13): 2784-92.

US 2007/10504A1 (2007). "Polymorphic and Amorphous salt forms of squalamine dilactate" Chellquist, Doubleday, Gilbert, Zhang, McLane, Armbruster, Levitt.

U.S. Pat. No. 5,763,430, for "Method of treating a viral infection by administering a steroid compound", to Zasloff, issued 1998.

U.S. Pat. No. 6,596,712, for "Treatment of carcinomas using squalamine in combination with other anticancer agents or modalities" Zasloff, Williams, Sokoloff, issued 2003.

U.S. Pat. No. 6,962,909, for "Treatment of neovascularization disorders with squalamine", to Zasloff, Shinnar, Kinney, Jones, issued 2005.

Zasloff, M., J. I. Williams, et al. (2001). "A spermine-coupled cholesterol metabolite from the shark with potent appetite suppressant and antidiabetic properties." Int J Obes Relat Metab Disord 25(5): 689-97.

What is claimed:

1. A pharmaceutical composition comprising:
   (a) at least one pharmaceutical grade aminosterol, wherein the aminosterol is selected from the group consisting of squalamine, Aminosterol 1436, a pharmaceutically acceptable salt thereof, and any combination thereof; and
   (b) at least one phosphate selected from the group consisting of an inorganic phosphate, an inorganic pyrophosphate, and an organic phosphate,
   wherein the aminosterol is formulated as a weakly water soluble salt of the phosphate.

2. The composition of claim 1, wherein the phosphate is an inorganic polyphosphate, and the number of phosphates can range from 3 to 400.

3. The composition of claim 1, wherein the phosphate is an organic phosphate which comprises glycerol 2 phosphate.

4. The composition of claim 1, wherein the aminosterol is squalamine or a pharmaceutically acceptable salt thereof.

5. The composition of claim 1, wherein the composition is formulated:
   (a) for routes of administration selected from the group consisting of oral, pulmonary, rectal, colonic, intracisternal, intravaginal, intraperitoneal, intravenous, subcutaneous, intramuscular, nebulization, inhalation, ocular, otic, local, buccal and nasal administration;
   (b) for a topical route of administration;
   (c) for parenteral administration;
   (d) into a dosage form selected from the group consisting of liquid dispersions, gels, aerosols, ointments, creams, lyophilized formulations, tablets, capsules; or
   (e) into a dosage form selected from the group consisting of controlled release formulations, fast melt formulations, delayed release formulations, extended release formulations, pulsatile release formulations, and mixed immediate release and controlled release formulations.

6. The composition of claim 1, wherein the composition further comprises at least one additional active agent.

7. The composition of claim 6, wherein the additional active agent is selected from the group consisting of:
   (a) an antiretroviral agent;
   (b) nucleoside or nucleotide reverse transcriptase inhibitors;
   (c) non-nucleoside reverse transcriptase inhibitors;
   (d) nucleotide or nucleoside analogues;
   (e) protease inhibitors;
   (f) drugs based on "antisense" molecules;
   (g) ribozyme antivirals;
   (h) assembly inhibitors;
   (i) release phase inhibitors;
   (j) drugs which stimulate the immune system;
   (k) fusion inhibitors/gp41 binders;
   (l) fusion inhibitors/chemokine receptor antagonists;
   (m) integrase inhibitors;
   (n) hydroxyurea-like compounds;
   (o) inhibitors of viral integrase;
   (p) inhibitors of viral genome nuclear translocation;
   (q) inhibitors of HIV entry;
   (r) nucleocapsid zinc finger inhibitors;
   (s) targets of HIV Tat and Rev;
   (t) pharmacoenhancers;
   (u) cytokines;
   (v) lymphokines;

(w) an anti-inflammatory agent;
(x) antibiotic;
(y) antifungal, antiyeast, and/or antimold agent;
(z) anticancer agent;
(aa) weight loss agent; and
(bb) any combination thereof.

8. The composition of claim 1, further comprising at least one adjuvant.

9. The composition of claim 8, wherein the adjuvant is selected from the group consisting of cytokines, IL2, IL3, IL4, IL5, IL6, IL7, IL8, IL-9, IL10, IL-11, IL12, IL13, IL-14, IL15, IIL16, IL-17, IL-18, IL-19, IL-20, IL-21, anti-CD40, CD40L, IFN-gamma, TNF-alpha, IL-Ialpha, IL-lbeta, alum, Lipid A, monophosphoryl lipid A, bacterial products, endotoxins, cholesterol, fatty acids, aliphatic amines, paraffinic oils, vegetable oils, threonyl derivative, muramyl dipeptide, alum plus deoxycholate MTP-PE, QS21, BCG, MPL, nonviable preparations of *Corynebacterium*, parvum, Monophosphoryl lipid immunomodulator, QS-18, CRL1005, Aluminum salts, MF-59, and Virosomal adjuvant technology.

10. The composition of claim 1, wherein the composition further comprises at least one antigen capable of eliciting an immune response.

11. The composition of claim 10, wherein the antigen is selected from the group consisting of viral and prion antigens.

12. The composition of claim 1, wherein the squalamine salt is in the form of a particulate suspension varying in particle size from between about 0.1 to about 100 microns.

13. The composition of claim 1 further comprising at least one pharmaceutically acceptable excipient.

14. The composition of claim 1 formulated as an oral tablet or capsule.

15. The composition of claim 4, wherein the aminosterol is Aminosterol 1436.

* * * * *